US012715826B2

(12) United States Patent
Marks et al.

(10) Patent No.: US 12,715,826 B2
(45) Date of Patent: Aug. 25, 2026

(54) CATALYTIC HYDROGENOLYSIS OF A POLYMER

(71) Applicant: NORTHWESTERN UNIVERSITY, Evanston, IL (US)

(72) Inventors: Tobin Jay Marks, Evanston, IL (US); Yosi Kratish, Evanston, IL (US); Alexander Heath Mason, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 253 days.

(21) Appl. No.: 18/580,514

(22) PCT Filed: Jul. 20, 2022

(86) PCT No.: PCT/US2022/037670
§ 371 (c)(1),
(2) Date: Jan. 22, 2024

(87) PCT Pub. No.: WO2023/003930
PCT Pub. Date: Jan. 26, 2023

(65) Prior Publication Data

US 2025/0243134 A1 Jul. 31, 2025

Related U.S. Application Data

(60) Provisional application No. 63/223,583, filed on Jul. 20, 2021.

(51) Int. Cl.
*C07C 4/22* (2006.01)
*B01J 27/053* (2006.01)
(Continued)

(52) U.S. Cl.
CPC ............... *C07C 4/22* (2013.01); *B01J 27/053* (2013.01); *B01J 31/122* (2013.01); *B01J 31/26* (2013.01);
(Continued)

(58) Field of Classification Search
CPC ........ B01J 27/053; B01J 31/122; B01J 31/26; B01J 2231/641; B01J 2531/48;
(Continued)

(56) References Cited

U.S. PATENT DOCUMENTS 6,171,475 B1 * 1/2001 Dufaud .................... C10G 1/10
208/111.1

FOREIGN PATENT DOCUMENTS

JP H11508936 A 8/1999

OTHER PUBLICATIONS

Dufaud, V. and Basset, J.-M., "Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization" (Year: 1998).*
(Continued)

*Primary Examiner* — James C Goloboy
(74) *Attorney, Agent, or Firm* — Dinsmore & Shohl LLP

(57) ABSTRACT

Provided is a process for hydrogenolysis of a polymer that includes providing in a reactor the polymer, hydrogen gas and a supported organometallic catalyst. The supported organometallic catalyst formed from an organometallic complex precatalyst and an acidic metal oxide support. The polymer is reacted with the supported organometallic catalyst in the presence of the hydrogen gas at a predetermined temperature in the reactor to produce a reduced polymer product having a weight average molecular weight less than the polymer.

19 Claims, 8 Drawing Sheets

Weakly Brønsted acidic hydroxylated oxide support

Covalent metal - surface interaction

(51) Int. Cl.
*B01J 31/12* (2006.01)
*B01J 31/26* (2006.01)

(52) U.S. Cl.
CPC ...... *B01J 2231/641* (2013.01); *B01J 2531/48* (2013.01); *B01J 2531/49* (2013.01); *B01J 2531/57* (2013.01); *B01J 2531/58* (2013.01); *B01J 2531/64* (2013.01); *B01J 2531/66* (2013.01); *Y02W 30/62* (2015.05)

(58) Field of Classification Search
CPC ......................... B01J 2531/49; B01J 2531/57; B01J 2531/58; B01J 2531/64; B01J 2531/66; C07C 4/22; Y02W 30/62
See application file for complete search history.

(56) References Cited

OTHER PUBLICATIONS (Box U continued) Angew. Chem. Int. Ed. 1998, 37, 806-810 (Year: 1998).*

Nicholas, C.P., Ahn, H., Marks, T.J., “Synthesis, Spectroscopy, and Catalytic Properties of Cationic Organozirconium Adsorbates on “Super Acidic” Sulfated Alumina. “Single-Site” Heterogeneous Catalysts with Virtually 100 Active Sites”, J. Am. Chem. Soc. 2003, 125, 14, 4325-4331 (Year: 2003).*

Norsic et al., “Low temperature hydrogenolysis of waxes to diesel range gasoline and light alkanes: Comparison of catalytic properties of group 4, 5, and 6 metal hydrides supported on silica-alumina”, Catal. Sci. Technol., 2012, 2, 215-219 (Year: 2012).*

International Search Report & Written Opinion for related PCT Application No. PCT/US2022/037670, dated Dec. 16, 2022, 12 pages.

Dufaud, V., et al., “Catalytic Hydrogenolysis at Low Temperature and Pressure of Polyethylene and Polypropylene to Diesels or Lower Alcanes by a Zirconium Hydride Supported on Silica-Alumina: A Step Toward Polyolefin Degredation by the Microscopic Reverse of Ziegler-Natta Polymerization”, Angewandte Chemie International Edition, Verlag Chemie, Nov. 7, 1997, pp. 806-809.

Norsic, Sebastien, et al., “Low Temperature Hydrogenolysis of Waxes to Diesel Range Gasoline and Light Alkanes: Comparison of Catalytic Properties of Group 4, 5 and 6 Metal Hydrides Supported on Silica-alumina”, Catalysis Science & Technology, vol. 2, No. 1, Jan. 1, 2012, pp. 215-219.

Nicholas, Christopher P., et al., “Synthesis, Spectroscopy, and Catalytic Properties of Cationic Organozirconium Adsorbates on “Super Acidic” Sulfated Alumina. “Single-Site” Heterogeneous Catalysts with Virtually 100% Active Sites”, Journal of the American Chemical Society, American Chemical Society, vol. 125, No. 4, Apr. 9, 2003, pp. 4325-4331.

Japanese Office Action dated Feb. 25, 2026, pertaining to JP Patent Application No. 2024-503521, 6 pgs.

* cited by examiner

Weakly Brønsted acidic hydroxylated oxide support

Covalent metal - surface interaction

Highly Brønsted acidic sulfated oxide support

Largely electrostatic metal - surface interaction, enhanced electrophilicty

CATALYTIC HYDROGENOLYSIS OF A POLYMER

CLAIM OF PRIORITY

This application is a National Stage Application under 35 U.S.C. § 371 of International Application No. PCT/US2022/037670, filed on Jul. 20, 2022, which claims the benefit of U.S. Provisional Application No. 63/223,583, filed on Jul. 20, 2021, the entire contents of which are incorporated herein by reference in its entirety.

REFERENCE TO GOVERNMENT RIGHTS

This invention was made with government support under DE-FG02-03ER15457 awarded by the Department of Energy. The government has certain rights in the invention.

BACKGROUND

The accumulation of consumer polymer waste has become a growing concern, given the severe detrimental environmental impact. Despite a heavy societal dependence on these materials, less than 10% of consumer polymers in the United States are recycled, with most accumulating in landfills. The largest share of these waste polymers is polypropylene (PP) and polyethylene (PE) based materials, and currently the small portion of these that are recycled is largely done so by mechanical means. However, recycled polymers are always less valuable than virgin polymer (made directly from the pure monomer). Accordingly, efforts have been mounting to investigate processes which produce valuable polymer materials from waste consumer polymers.

SUMMARY

The present disclosure provides for supported organometallic catalysts and processes using the supported organometallic catalysts for depolymerizing polymers via hydrogenolysis. Hydrogenolysis is a chemical reaction that involves the catalytic cleavage of carbon-carbon or carbon-heteroatom single bonds with hydrogen ($H_2$). The present processes may be used to convert long carbon chains of polymers (e.g., polypropylene or polyethylene), including polyolefins, to products having lower molecular weights as compared to the starting polymer.

The supported organometallic catalysts of the present disclosure are highly electrophilic, formally cationic earth-abundant single-site organometallic catalysts that are chemisorbed on an acidic metal oxide support (e.g., a highly Brønsted acidic sulfated alumina support). The supported organometallic catalysts of the present disclosure mediate the rapid hydrogenolytic cleavage of molecular and macromolecular saturated hydrocarbons under mild conditions, with catalytic onset as low as 90° C./0.5 atm $H_2$ with 0.02 mol % catalyst loading. For polyethylene, quantitative hydrogenolysis to light hydrocarbons (e.g., hydrocarbons of less than C9) proceeds within 48 minutes with an activity of greater than 4000 mol ($CH_2$ units)·mol $(Zr)^{-1}$·$h^{-1}$ at 200° C./2 atm $H_2$ pressure. Under similar solventless conditions, polyethylene-co-1-octene, isotactic polypropylene, and a post-consumer sandwich bag are rapidly hydrogenolyzed to low molecular weight hydrocarbons. Such surprising results may find meaningful use in helping to decrease fossil fuels reliance and address the recycling and repurposing of the abundance of plastic waste in today society.

Embodiments of the present disclosure provide for a process for hydrogenolysis of a polymer, as provided herein. The process includes providing in a reactor the polymer, hydrogen gas ($H_2$) and the supported organometallic catalyst of the present disclosure. The supported organometallic catalyst is formed from an organometallic complex precatalyst of Formula I and an acidic metal oxide support. The organometallic complex precatalyst of Formula I is:

$$MR_mL_x, \qquad \text{Formula I}$$

where m is 0 to 6; x is 0 to 6; M is a transition metal selected from the group consisting of transition metal groups 3 through 8; R is independently selected from the group consisting of H, a C1 to C8 hydrocarbyl or a halogen; and each L is independently selected from the group consisting of a C1 to C12 substituted or unsubstituted hydrocarbyl. The value of m and x will depend upon the oxidation state of M. The process further includes reacting the polymer with the supported organometallic catalyst while stirring the mixture in the presence of the hydrogen gas at a predetermined temperature in the reactor to produce a reduced polymer product having a weight average molecular weight less than the polymer.

For the various embodiments, M is selected from the group consisting of transition metal groups 4, 5, 6 or 8. For the various embodiments, M is selected from the group consisting of Ti, Zr, Hf, V, Nb, Ta, Cr, Mo, W, Fe, Ru, Co or Ni. Preferably, M is selected from the group consisting of transition metal groups 4, 5 or 6. Preferably, M is selected from the group consisting of Ti, Zr, Hf, Nb, Ta, Mo or W. Most preferably, M is from transition metal group 4 selected from the group consisting of Ti, Zr or Hf. For the various embodiments, M is also preferably selected from the group consisting of Zr or Hf, where m is 0 and each L is independently selected from a C1 to C12 alkyl.

For the various embodiments, the hydrocarbyl for L in Formula I is independently selected from the group consisting of a C1 to C10 alkyl, a C2 to C10 alkenyl or a C5 to C10 aryl. As used herein, aryl can include multiple ring structures (e.g., fused rings). Preferably, L in Formula I is neopentyl (e.g., 2,2-dimethylpropyl).

For the various embodiments, the acidic metal oxide support is a sulfated metal oxide (e.g., a highly Brønsted acidic oxide). For the various embodiments, the sulfated metal oxide is selected from the group consisting of a sulfated aluminum oxide, zirconium (IV) oxide, tin (IV) oxide, hafnium (IV) oxide, titanium (IV) oxide; iron (III) oxide, zinc (II) oxide; silica oxide or combinations thereof.

For the various embodiments, the predetermined temperature for the process is from 60° C. to 300° C. Preferably, the predetermined temperature for the process is from 90° C. to 200° C. More preferably, the predetermined temperature for the process is from 110° C. to 150° C.

For the various embodiments, reacting the polymer can include stirring the polymer with the supported organometallic catalyst in the presence of the hydrogen gas at a rate of 500-3000 rpm. Such stirring of the supported organometallic catalyst and the polymer better ensures thorough mixing of the polymer and the supported organometallic catalyst.

For the various embodiments, the reduced polymer product produced according to the process of the present disclosure has a weight average molecular weight less than the starting polymer. For the various embodiments, the reduced polymer product is at least one of a volatile product, an oil product or a wax product, each as defined herein. For the various embodiments, the reduced polymer product includes less than 5 weight percent of the wax product based on the total weight of the reduced polymer product.

For the various embodiments, the polymer is selected from the group consisting of a polyolefin, a polymer formed by polymerization of aromatic alkenes or those formed by polymerization of conjugated dienes. For the various embodiments, the polyolefin is preferably selected from the group consisting of polyethylene, polypropylene, a linear or branched C4-C12 mono-olefin, a copolymer thereof, or combinations thereof. More preferably, the polyolefin is selected from the group consisting of polyethylene, polypropylene or copolymers thereof.

For the various embodiments, providing hydrogen gas to the reactor includes providing the hydrogen gas at a pressure of 0.1 atm to 100 atm to the reactor. Preferably, providing hydrogen gas to the reactor includes providing the hydrogen gas at a pressure of 0.2 atm to 50 atm to the reactor. More preferably, providing hydrogen gas to the reactor includes providing the hydrogen gas at a pressure of 0.5 atm to 4 atm to the reactor. For the various embodiments, reacting the polymer with the supported organometallic catalyst in the presence of the hydrogen gas at the predetermined temperature is for a time from 0.25 hour to 24 hours. For the various embodiments, providing in the reactor the supported organometallic catalyst includes providing from 0.01 mole percent (mol. %) to 0.9 mol. % of M based on the monomer units of the polymer (e.g., $—C_2H_4—$ monomer units of polyethylene).

For the various embodiments, the supported organometallic catalyst is represented by Formula II:

$$L_{y\text{-}x}R_{x\text{-}z}M^{n+} \underline{\ldots} O^- \text{ (acidic metal oxide support)} \qquad \text{Formula II}$$

where M is selected from the group consisting of Ti, Zr, Hf, V, Nb, Ta, Cr, Mo, W, Fe, Ru, Co or Ni; R is independently selected from hydrogen, a halogen or L; each L is independently selected from a C1 to C12 saturated or unsaturated hydrocarbyl, or a C1 to C12 silyl hydrocarbyl; n is 1; y is 3; x is 2 or 1; and z is 1 or 0. In some embodiments, n can also be 2 or 3 when M is not in its highest possible oxidation state. For example, when M is either Co or Fe then n can be 2, x can be 1 and z can be 1 to give $L_2Co^{2+} \underline{\ldots} O^-$ (acidic metal oxide support) or $L_2Fe^{2+} \underline{\ldots} O^-$ (acidic metal oxide support). In Formula II, "..." represents the electrostatic, noncovalent bond between $M^{n+}$ and $O^-$ of the support material, and "$\underline{\ldots} O^-$" represents the weak Lewis basic support material after deprotonation. Preferably, for Formula II M is selected from the group consisting of Ti, Zr or Hf, each L is a C3-C8 saturated or unsaturated hydrocarbyl, n is 1, y is 3, x=1 and z=1. More preferably, for Formula II M is selected from the group consisting of Ti, Zr or Hf; each L is a C5 saturated hydrocarbyl, n is 1, y is 3 and x=1 and z=1.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

Figure 1A:
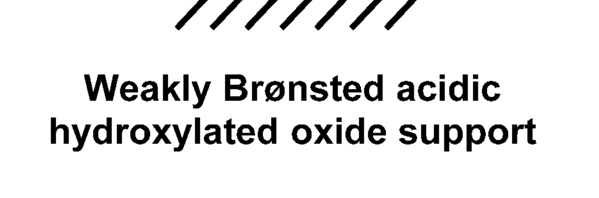
FIG. 1A. An example of existing catalysts composed of a metal alkyl covalently bound to a strongly Lewis-basic oxide support material.

The present disclosure provides for depolymerizing a polymer using a supported organometallic catalyst via hydrogenolysis. Hydrogenolysis is a chemical reaction that involves the catalytic cleavage of carbon-carbon or carbon-heteroatom single bonds with hydrogen ($H_2$). In the present processes, the polymer is combined with hydrogen and the supported organometallic catalyst of the present disclosure under relatively mild conditions selected to induce hydrogenolysis of the polymer to provide fragments thereof, i.e., lower molecular weight products. The present processes may be used to convert long carbon chains of polymers, including polyolefins (e.g., polypropylene or polyethylene), to products having lower molecular weights as compared to the starting polymer.

Compared to existing processes for depolymerizing polymers, the present disclosure make use of supported organometallic catalysts under generally mild conditions such as lower temperatures, lower $H_2$ pressures, low catalyst loadings all while achieving fast reaction rates. In addition, although a solvent may be used none is required in the process of the present disclosure. At the same time, embodiments of the present disclosure are able to achieve extremely high activities, e.g., two orders of magnitude greater than existing catalysts using similar conditions.

The supported organometallic catalysts of the present disclosure are highly electrophilic, formally cationic earth-abundant single-site organometallic catalysts that are chemisorbed on an acidic metal oxide support (e.g., a highly Brønsted acidic sulfated alumina support). The supported organometallic catalysts of the present disclosure mediate the rapid hydrogenolytic cleavage of molecular and macromolecular hydrocarbons (e.g., saturated hydrocarbons) under mild conditions, with catalytic onset as low as 90° C./0.5 atm $H_2$ with 0.02 mol % catalyst loading. For polyethylene, quantitative hydrogenolysis to volatile hydrocarbons (e.g., light hydrocarbons of less than C9) proceeds within 48 minutes with an activity of greater than 4000 mol $(CH_2$ units)·mol $(Zr)^{-1}\cdot h^{-1}$ at 200° C./2 atm $H_2$ pressure. Under similar solventless conditions, polyethylene-co-1-octene, isotactic polypropylene, and a post-consumer sandwich bag (e.g., low-density polyethylene) are rapidly hydrogenolyzed to products having lower molecular weights as compared to the starting polymer. Such surprising results may find meaningful use in helping to decrease the reliance on fossil fuels while addressing recycling and repurposing aspects of the abundance of plastic waste in today society.

Definitions

Before the present compounds, components, compositions, and/or methods are disclosed and described, it is to be understood that unless otherwise indicated this disclosure is not limited to specific compounds, components, compositions, reactants, reaction conditions, moieties, ligands, structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an," and "the" include plural referents unless otherwise specified. Thus, for example, reference to "a reduced polymer product" can include more than one reduced polymer product thereby providing for "reduced polymer products." Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein a "polymer" includes linear or branched homopolymers or linear or branched copolymers. The polymer has two or more of the same or different monomer units (i.e., mers) derived from one or more different monomers, e.g., homopolymers, copolymers, terpolymers, etc. A "homopolymer" is a polymer having polymer units that are all the same (e.g., 100 wt % of the polymer units are derived from ethylene or 100 wt % of the polymer units derived from propylene). A "copolymer" is a polymer having two or more polymer units that are different from each other, such as, for example, those made by the copolymerization of ethylene with C3-C10 alpha olefins, or propylene with ethylene and/or C4-C10 alpha olefins. A "terpolymer" is a polymer having three polymer units that are different from each other. "Different" in reference to polymer units indicates that the polymer units differ from each other by at least one atom or are different isometrically. Accordingly, the definition of copolymer, as used herein, includes terpolymers and the like.

Embodiments provide that the polymer can be a polyolefin. A polyolefin includes homopolymers and/or copolymers made from olefin monomers such as ethylene, i.e., polyethylene, propylene, i.e., polypropylene, and linear or branched higher alpha-olefin C4-C12 monomers (e.g., linear or branched C4-C12 mono-olefins). Examples of higher alpha-olefin monomers include, but are not limited to, 1-butene, 1-pentene, 1-hexene, 4-methyl-1-pentene, 1-octene, and 3,5,5-trimethyl-1-hexene. Examples of polyolefins include ethylene-based polymers, include homopolymers of polyethylene (e.g., formed from 100 wt % ethylene) and those having at least 50 wt % ethylene (e.g., a polyethylene copolymer), ethylene-1-butene, ethylene-1-hexene, and ethylene-1-octene copolymers, among others. Examples of polyolefins include propylene-based polymers, include homopolymers of polypropylene (e.g., formed from 100 wt % propylene) and those having at least 50 wt % propylene (e.g., a polypropylene copolymer), including propylene-1-butene, propylene-1-hexene, and propylene-1-octene copolymers, among others. Other olefins that may be utilized include ethylenically unsaturated monomers, diolefins having 4 to 18 carbon atoms, conjugated dienes or nonconjugated dienes, polyenes, vinyl monomers, aromatic alkenes and cyclic olefins, for example. Examples of the monomers may include, but are not limited to, norbornene, norbornadiene, isobutylene, isoprene, vinylbenzocyclobutane, styrenes, alkyl substituted styrene, ethylidene norbornene, dicyclopentadiene and cyclopentene. In a number of embodiments, a copolymer of ethylene can be produced, where with ethylene, a comonomer having at least one alpha-olefin having from 4 to 15 carbon atoms, preferably from 4 to 12 carbon atoms, and most preferably from 4 to 8 carbon atoms, is polymerized, e.g., in a gas phase polymerization process. Similarly, in a number of embodiments, a copolymer of propylene can be produced, where with propylene, a comonomer having at least one alpha-olefin having from 4 to 15 carbon atoms, preferably from 4 to 12 carbon atoms, and most preferably from 4 to 8 carbon atoms, is polymerized, e.g., in a gas phase polymerization process. In another embodiment, ethylene and/or propylene can be polymerized with at least two different comonomers, optionally one of which may be a diene, to make a terpolymer.

As used herein, the transition metal groups discussed and claimed herein are found in Groups 4-10 of the IUPAC Period Table of the Elements, 4 May 2022.

As used herein, the term "hydrocarbyl" refers to univalent groups formed by removing a hydrogen atom from a hydrocarbon, e.g., methyl, ethyl, propyl, butyl, pentyl, hexyl, heptyl, octyl, cyclopentyl, cyclohexyl, cyclohexylmethyl, phenyl, benzyl, naphthyl, among others. Illustrative hydrocarbyls include alkyls, alkenyls, and aryls. The hydrocarbyl may be linear, branched, or cyclic.

As used herein, the term "substituted", e.g., "substituted hydrocarbyl" indicates that the group following that term possesses at least one moiety in place of one or more hydrogens in any position, the moieties selected from such groups as halogen radicals, hydroxyl groups, carbonyl groups, carboxyl groups, amine groups, phosphine groups, alkoxy groups, phenyl groups, naphthyl groups, (C1 to C20)alkyl groups, (C2 to C10)alkenyl groups, and combinations thereof, unless another type of substitution is specifically stated, such as "alkyl-substituted" or "substituted by aryl". When the term "substituted" introduces a list of possible substituted groups, it is intended that the term apply to every member of that group. That is, the phrase "substituted alkyl, alkenyl and aryl" is to be interpreted as "substituted alkyl, substituted alkenyl and substituted aryl."

When the term "sulfated" introduces a list of possible sulfated metal oxides it is intended that the term apply to every member of that group. That is, the phrase "sulfated aluminum oxide, zirconium (IV) oxide, tin (IV) oxide, hafnium (IV) oxide, titanium (IV) oxide; iron (III) oxide, zinc (II) oxide; silica oxide, or combinations thereof" is to be interpreted as "sulfated aluminum oxide, sulfated zirconium (IV) oxide, sulfated tin (IV) oxide, sulfated hafnium (IV) oxide, sulfated titanium (IV) oxide; sulfated iron (III) oxide, sulfated zinc (II) oxide; sulfated silica oxide, or combinations thereof."

As used herein, the term "alkyl" refers to a branched or unbranched (e.g., linear), cyclic or acyclic saturated hydrocarbyl radical that are deficient by one hydrogen typically, although not necessarily, containing 1 to 50 carbon atoms, more preferably 1 to 20 carbon atoms, most preferably 1 to 10 carbon atoms, e.g., methyl, ethyl, n-propyl, isopropyl, n-butyl, isobutyl, sec-butyl, t-butyl, pentyl, hexyl, octyl, decyl, as well as cycloalkyl groups, e.g., cyclopropyl, cyclobutyl, cyclopentyl, cyclohexyl, cyclopentylmethyl, and cyclohexylethyl.

The term "alkenyl" as used herein refers to a branched or unbranched, cyclic or acyclic hydrocarbyl radical containing at least one double bond and typically, although not necessarily, containing 2 to 50 carbon atoms, more preferably 2 to 20 carbon atoms, most preferably 2 to 10 carbon atoms, e.g., ethenyl, n-propenyl, isopropenyl, n-butenyl, isobutenyl, 4-octenyl, 2-decenyl, cyclopentenyl, cyclopentadienyl, cyclohexenyl, and cyclohexadienyl, among others.

The term "aromatic" is used in its usual sense, including unsaturation that is essentially delocalized across several bonds around a ring. The term "aromatic" as used herein refers to a group containing an aromatic ring or ring system typically, although not necessarily, containing 5 to 50 carbon atoms, preferably 5 to 25 carbon atoms, more preferably 5 to 16 carbon atoms. Typical neutral unsubstituted aromatic compounds include benzene, naphthalene, anthracene, phenanthrene, pyridine, pyrazine, imidazole, pyrazole, oxazole, thiophene, pyrrole, triazole, indole, and benzimidazole. Typical charged unsubstituted aromatic compounds include cyclopropenyl cation and cyclopentadienyl anion.

As used herein, the term "aryl" refers to groups containing an aromatic ring or ring system typically, although not necessarily, containing 5 to 50 carbon atoms, preferably 5 to 20 carbon atoms, more preferably 5 to 10 carbon atoms. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, terphenyl, anthracenyl, phenanthrenyl, pyridinyl, pyrazinyl, imidazolyl, pyrazolyl, oxazolyl, thienyl, pyrrolyl, triazolyl, indolyl, and benzimidazolyl. The aryl groups may be unsubstituted or may be substituted with halogen, preferably fluorine, chlorine, or bromine, more preferably fluorine or bromine, even more preferably fluorine; hydrocarbyl, such as alkyl, alkenyl, or alkynyl, heterohydrocarbyl; or heteroatom groups. In particular embodiments, aryl substituents (substituents on the aryl group) include 1 to 40 atoms other than hydrogen, preferably 1 to 20 atoms other than hydrogen, and more preferably 1 to 10 atoms other than hydrogen. Substituted aryl groups include tolyl (methylphenyl), xylyl (dimethylphenyl), mesityl (trimethylphenyl), ethylphenyl, styryl, allylphenyl, propynylphenyl, chlorophenyl, fluorophenyl, difluorophenyl, trifluorophenyl, tetrafluorophenyl, pentafluorophenyl, pentafluorobiphenyl, methoxyphenyl, ethoxyphenyl, dimethoxyphenyl, trifluoromethylphenyl, bis(trifluoromethyl)phenyl, dimethylaminophenyl, dimethylaminoethylphenyl, phenoxyphenyl, methylcarboxyphenyl, ethylcarboxyphenyl, methoxynaphthyl, nitrophenyl, dinitrophenyl, cyanophenyl, dicyanophenyl, chloropyridinyl, methylimidazolyl, phenylpyrrolyl, and ethylthienyl.

As used herein, the term "halogen" refers to fluorine, chlorine, bromine and iodine.

As used herein the term "silyl hydrocarbyl" refers to an —$SiR^1R^2R^3$ radical, where each of $R^1$, $R^2$, and $R^3$ is independently selected from the group consisting of hydride and optionally substituted alkyl, alkenyl, alkynyl, heteroatom containing alkyl, heteroatom-containing alkenyl, heteroatom-containing alkynyl, aryl, heteroaryl, alkoxy, aryloxy, amino, silyl and combinations thereof. In the "silyl hydrocarbyl" the silicon atom may be directly bonded to the metal or a carbon atom of the "silyl hydrocarbyl" may be directly bonded to the metal.

The term "saturated" means lacking a carbon-carbon double bond, a carbon-carbon triple bond, and (in heteroatom-containing groups) carbon-nitrogen, carbon-phosphorous, and carbon-silicon double or triple bonds.

As used herein, the term "weight average molecular weight" (Mw) is the mass of individual polymer chains, which contributes to the overall molecular weight of the polymer, where Mw is calculated, as known in the art, from the weight fraction distribution of different sized molecules. Mw can be measured by gel permeation chromatography (GPC), osmometry, light scattering, viscometry, cryoscopy, ebulliometry, ultracentrifugation, mass spectrometry, and end-group analysis as are known in the art.

As used here, the terms "volatile product" or "volatiles" refer to linear or branched (where possible) hydrocarbons having less than nine carbons (e.g., less than C9).

As used here, the terms "oil product" or "DCM Extract" refer to linear or branched hydrocarbons having nine to twenty-six carbons (e.g., C9-C26).

As used here, the terms "wax product" or "solids" refer to linear or branched hydrocarbons having twenty-seven to less than the number of carbons of the polymer from which the wax product is formed according to the present disclosure.

As used herein, the "~" symbol represents the word "approximately."

The abbreviation "atm" stands for atmosphere (1 atm=101.325 kPa); the abbreviation "mol" stands for mole; the abbreviation "° C." stands for degree Celsius; the abbreviation "kg" stands for kilogram; the abbreviation "L" stands for liter; the abbreviation "h" stands for hour; the abbreviation "min" stands for minute; the abbreviation "wt %" stands for weight percent; the abbreviation "ppm" stands for parts per million; abbreviation "mg" stands for milligram; "rpm" stands for revolutions per minute; the abbreviation "μm" stands for micrometers, or $10^{-6}$ meters.

The polymers which may be depolymerized via hydrogenolysis using the supported organometallic catalyst of the present disclosure can include polyolefins, which are formed by polymerizing olefins, e.g., ethylene, propylene, hexene, octene, and combinations thereof. As discussed herein, the olefin may be an alpha-olefin such that the polyolefin is a poly-alpha-olefin. For the various embodiments, the polymer is preferably selected from the group consisting of a polyolefin, a polymer formed by polymerization of aromatic alkenes, e.g., styrene, and those formed by polymerization of conjugated dienes, e.g., butadiene, isoprene, etc. For the various embodiments, the polyolefin is more preferably selected from the group consisting of polyethylene, polypropylene, a linear or branched C4-C12 mono-olefin, a copolymer thereof, or combinations thereof. Most preferably, the polyolefin is polyethylene and polypropylene, a copolymer thereof, or combinations thereof. The polymers may be linear or branched. The polymers may be homopolymers or copolymers. The polymers may have any tacticity and degree thereof, e.g., >90% isotactic, atactic or syndiotactic. The polymers may have various weight average molecular weights (Mw) as are known in the art for a variety of commercial products, e.g., ranging from 3 to 300 kg/mol.

Embodiments of the present disclosure provide for a process for hydrogenolysis of the polymer, as provided herein, using a supported organometallic catalyst. The supported organometallic catalyst is formed from a particular combination of an acidic metal oxide support and an organometallic complex precatalyst. As provided herein, the supported organometallic catalyst of the present disclosure has unexpectedly high activity in the hydrogenolysis of the disclosed polymers.

The hydrogenolysis process of the present disclosure includes providing in a reactor the polymer, hydrogen gas ($H_2$) and the supported organometallic catalyst. The supported organometallic catalyst is formed from an organometallic complex precatalyst of Formula I and an acidic metal oxide support. The organometallic complex precatalyst of Formula I is:

$$MR_mL_x, \quad \text{Formula I}$$

For Formula I, m is 0 to 6 and x is 0 to 6. As appreciated by one skilled in the art, the value of m and x will depend upon the formal oxidation state of M in Formula I. For example, when M is a group 4 transition metal (e.g., Zr, Hf or Ti) m can be zero (0) and x can be 4. In an additional example, when M is a group 5 transition metal (e.g., Nb or Ta) m can be 1 or 2 and x can be 3. In a further example, when M is a group 6 transition metal (e.g., W or Mo) m can be 1 or 2 and x can be 4. Other values for m and x are of course possible.

For the various embodiments, M is a transition metal selected from the group consisting of transition metal groups 3 through 8. For the various embodiments, M is preferably selected from the group consisting of transition metal groups 4, 5, 6 or 8. More preferably, M is selected from the group consisting of transition metal groups 4, 5 or 6. Specific examples of M include those selected from the group consisting of Ti, Zr, Hf, V, Nb, Ta, Cr, Mo, W, Fe, Ru, Co or Ni. Preferably, M is selected from the group consisting of Ti, Zr, Hf, Nb, Ta, Mo or W. Most preferably, M is from transition metal group 4 selected from the group consisting of Ti, Zr or Hf.

For the various embodiments, R is independently selected from the group consisting of H, a C1 to C8 hydrocarbyl or a halogen. Preferably, when R is a halogen it is fluorine. Preferably, when R is a hydrocarbyl it is a C4 to C8 hydrocarbyl. More preferably, when R is a hydrocarbyl it is a C5 to C6 hydrocarbyl. Most preferably, when R is a hydrocarbyl it is a C5 hydrocarbyl, where when M is a group 5 transition metal the (═CHtBu) moiety is preferred and when M is a group 6 transition metal the (≡CtBu) moiety is preferred.

For the various embodiments, each L is independently selected from the group consisting of a C1 to C12 substituted or unsubstituted hydrocarbyl. For the various embodiments, the hydrocarbyl for L in Formula I is independently selected from the group consisting of a C1 to C10 alkyl, a C2 to C10 alkenyl or a C5 to C10 aryl. As used herein, aryl can include multiple ring structures (e.g., fused rings). Preferably, for the various embodiments the hydrocarbyl for L in Formula I is independently selected from the group consisting of a C4 to C7 alkyl, a C3 to C7 alkenyl or a C5 to C8 aryl. Most preferably, L in Formula I is neopentyl (e.g., 2,2-dimethylpropyl, abbreviated herein as "Np"). For the various embodiments, each L may be the same or different.

By way of more specific embodiments, M is preferably selected from the group consisting of Zr or Hf; m is 0 and each L is independently selected from a C1 to C12 alkyl, where L is preferably neopentyl (e.g., 2,2-dimethylpropyl). In additional examples, the organometallic complex precatalyst of Formula I can include, but are not limited to, $ZrNp_4$ (M=Zr, m=0, x=4 and L=Np), $HfNp_4$ (M=Hf, m=0, x=4 and L=Np), $TiNp_4$ (M=Ti, m=0, x=4 and L=Np), $NbF_2Np_3$ (M=Nb, m=2, R=F, x=3 and L=Np), Ta(≡CH$^t$Bu)$Np_3$ (M=Ta, m=1, R=(≡CH$^t$Bu), x=3 and L=Np), Nb(CH$^t$Bu)$Np_3$ (M=Nb, m=1, R=(═CH$^t$Bu), x=3 and L=Np), W(C$^t$Bu)$Np_3$ (M=W, m=1, R=(≡CtBu), x=3 and L=Np), and Mo(C$^t$Bu)$Np_3$ (M=Mo, m=1, R=(≡CtBu), x=3 and L=Np). Other exemplary organometallic complex precatalysts of Formula I can include $MB_{Z4}$ (Bz=benzyl; M=Ti, Zr, Hf); $MAllyl_4$ (M=Ti, Zr, Hf); $CrNp_4$; $FeNp_4$; and $CoNp_3$.

For the various embodiments, the metal oxide used in forming the acidic metal oxide support can be selected from the group consisting of aluminum oxide ($Al_2O_3$), silicon oxide (e.g., $SiO_2$), nickel (II) oxide, zirconium (IV) oxide, tin (IV) oxide, hafnium (IV) oxide, titanium (IV) oxide; iron (III) oxide, zinc (II) oxide; or mixtures thereof. For the various embodiments, the acid used in forming the acidic metal oxide support can be selected from sulfuric acid, trifluoromethanesulfonic acid, fluorosulfonic acid, or fluorosulfonic acid+antimony pentfluoride ("magic acid"). For the various embodiments, the acidic metal oxide support is a highly Brønsted acidic oxide. Such oxides are generally classified as those having a Hammett acidity function (i.e., Ho) value$<-15$. Preferably, sulfated metal oxides may be used as the acidic metal oxide support. Illustrative sulfated metal oxides include sulfated alumina, sulfated silica, or combinations thereof. The zeolite H-ZSM-5 may be also used as the support material. In embodiments, the support material is sulfated alumina.

Forming the acidic metal oxide support can be accomplished in a number of ways. For example, under atmospheric conditions, the acid (e.g., 2.0 M sulfuric acid aqueous solution) can be added to and stirred with the metal oxide (e.g., aluminum oxide) for a reaction time of 15 to 90 minutes. The proportions (e.g., mole ratio acid:oxide) for the reaction mixture can vary from 5:1 to 1:5. After the reaction time the sulfated metal oxide is separated from the acid (e.g., by centrifugation) and rinsed with deionized (DI) water repeatedly until a pH of about 6 for the DI water of the rinse is achieved. The resulting acidic metal oxide is then dried at a temperature of 90 to 140° C. under vacuum for about 12 to 24 hours. The acidic metal oxide solids can be crushed (e.g., via mortar and pestle) and sieved to a desired mesh (e.g., 180 mesh, 80 μm). The acidic metal oxide can then be calcined (e.g., in a tube furnace) at a temperature of 400 to 650° C. under flowing $O_2$ (~2 L/min) for 2 to 4 hours, after which the acidic metal oxide is placed under vacuum (e.g., tube furnace interfaced to a high vacuum line and pumped down to a low vacuum, e.g., ~$10^{-6}$ Torr) for 1 h at a temperature of 300 to 450° C. The acidic metal oxide is then cooled under the vacuum and brought into an inert (e.g., argon) environment, where the acidic metal oxide can be removed and stored under an inert gas (e.g., argon).

For the various embodiments, the supported organometallic catalyst is formed from the organometallic complex precatalyst of Formula I and the acidic metal oxide support. Forming the supported organometallic catalyst can be accomplished through a chemisorption process (e.g., adsorption in which the adsorbed substance is held by electrostatic chemical bonds), as follows. The molar ratio of the organometallic complex precatalyst of Formula I and the acidic metal oxide support (varying from 1:20 to 5:20) is combined with a C4 to C8 organic solvent (e.g., n-pentane) at a temperature of 20 to 30° C. to form a slurry. The slurry is allowed to react for 30 minutes to 4 hours, after which time the resulting supported organometallic catalyst is filtered and washed with fresh organic solvent and dried under vacuum for at least one hour. The supported organometallic catalyst is stored under an inert atmosphere (e.g., argon).

For the various embodiments, the supported organometallic catalyst discussed herein is represented by Formula II:

$$L_{y-x}R_{x-z}M^{n+} \underline{\ldots} O^{-} \text{ (acidic metal oxide support)} \quad \text{Formula II}$$

where M is selected from the group consisting of Ti, Zr, Hf, V, Nb, Ta, Cr, Mo, W, Fe, Ru, Co or Ni; R is independently selected from hydrogen, a halogen or L; each L is independently selected from a C1 to C12 saturated or unsaturated hydrocarbyl, or a C1 to C12 silyl hydrocarbyl; n is 1; y is 3; x is 2 or 1; and z is 1 or 0. In some embodiments, n can also be 2 or 3 when M is not in its highest possible oxidation state. For example, when M is either Co or Fe then n can be 2, x can be 1 and z can be 1 to give $L_2Co^{2+}$ ... $O^-$ (acidic metal oxide support) or $L_2Fe^{2+}$ ... $O^-$ (acidic metal oxide support). In Formula II, " . . . " represents the electrostatic, noncovalent bond between $M^{n+}$ and $O^-$ of the support material, and "... O" represents the weak Lewis basic support material after deprotonation. Preferably, for Formula II M is selected from the group consisting of Ti, Zr or Hf; each L is a C3-C8 saturated or unsaturated hydrocarbyl, n is 1, y is 3, x is 1 and z is 1. More preferably, for Formula II M is selected from the group consisting of Ti, Zr or Hf, each L is a C5 saturated hydrocarbyl, n is 1, y is 3, x is 1 and z is 1. The supported organometallic catalyst may be where the acidic metal oxide support is a sulfated metal oxide support material and wherein M is Ti, Zr or Hf; L is neopentyl; n is 1, y is 3; x is 1; and z is 1. Preferably, when R is a halogen it is fluorine. Additional examples of the supported organometallic catalyst represented by Formula II include those where: M=Zr, L=Np, n=1, y=3, x=1 and z=1 so R is not present; M=Hf, L=Np, n=1, y=3, x=1 and z=1 so R is not present; M=Ti, L=Np, n=1, y=3, x=1 and z=1 so R is not present; M=Ta, L=Np, R=$CH^tBu$, n=1, y=3, x=2 and z=1; M=Nb, L=Np, R=F, n=1, y=3, x=2 and z=0; M=Nb, L=Np, R=$CH^tBu$, n=1, y=3, x=2 and z=1; M=W, L=Np, R=$C^tBu$, n=1, y=3, x=2 and z=1; and M=Ta, L=Np, R=$C^tBu$, n=1, y=3, x=2 and z=1.

The method of making the supported organometallic catalyst from the organometallic complex precatalyst of Formula I and the acidic metal oxide support is also described in the Example below. In particular, the use of the sulfuric acid treatment, calcination temperature, and inert solvent (e.g., dry hydrocarbon) in making the supported organometallic catalyst as described in the Example below are helpful to ensure the desired supported organometallic catalyst is achieved. In one embodiment, the supported organometallic catalyst may be represented by the formula $L_2M^+R$ . . . $O^-$ ... (acidic metal oxide support), wherein L and M are as defined herein; "+" represents the formal cationic charge on M; R is hydrogen or L; " . . . " represents the electrostatic, noncovalent bond between $M^+$ and $O^-$ of the support material; and "... O" represents the weak Lewis basic support material after deprotonation.

Figure 1B:
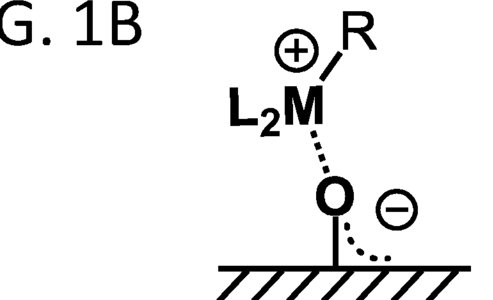
FIG. 1B. An example of present supported organometallic catalyst composed of a cationic metal alkyl on an extremely weakly Lewis-basic support with a loose, ionic metal-support interaction (i.e., the metal and the support material are noncovalently bound).

The supported organometallic catalyst of the present disclosure is different from existing catalysts which are represented by the formula shown in FIG. 1A. In particular, in the supported organometallic catalyst of the present disclosure, the M is formally cationic while in the conventional catalysts, the M is formally neutral. In addition, in the supported organometallic catalyst, the M is noncovalently/electrostatically bound to the support material, while in the existing catalysts, the M is covalently bound. These differences are illustrated in FIGS. 1A and 1B, where FIG. 1A represents the existing catalysts and FIG. 1B represents an example of the supported organometallic catalyst of the present disclosure.

The process further includes reacting the polymer, as provided herein, with the supported organometallic catalyst in the presence of the hydrogen gas at a predetermined temperature in the reactor to produce a reduced polymer product having a weight average molecular weight less than the polymer. For the various embodiments, the surface area of the polymer can be increased prior to or during the reaction through a size reducing operation. Such size reducing operations can include, but are not limited to, those that chop, shear, pulverize, shave and/or grate the polymer into pieces that are smaller than those before the size reducing operation.

The conditions used in the present processes include parameters such as the predetermined temperature, $H_2$ pressure, time, and metal loading provided by the supported organometallic catalyst. Generally, these parameters are selected such that the combination induces the desired hydrogenolysis reactions. Additionally, parameters may be tuned to achieve a desired product or yield thereof, a product distribution, activity, conversion of the polymer, or combinations thereof.

Illustrative predetermined temperatures include those in a range of from 60° C. to 300° C. Preferably, the predetermined temperature is from 90° C. to 200° C. More preferably, the predetermined temperature is from 110° C. to 150° C.

For the various embodiments, providing hydrogen gas to the reactor includes providing the hydrogen gas at a pressure of 0.1 atm to 100 atm to the reactor. Preferably, providing hydrogen gas to the reactor includes providing the hydrogen gas at a pressure of 0.2 atm to 50 atm to the reactor. More preferably, providing hydrogen gas to the reactor includes providing the hydrogen gas at a pressure of 0.5 atm to 4 atm to the reactor.

For the various embodiments, reacting the polymer can include stirring the polymer with the supported organometallic catalyst in the presence of the hydrogen gas at a rate of 500-3000 rpm. Such stirring of the supported organometallic catalyst and the polymer better ensures thorough mixing of the polymer and the supported organometallic catalyst.

For the various embodiments, providing in the reactor the supported organometallic catalyst includes providing from 0.01 mole percent (mol. %) to 0.9 mol. % of M based on monomer units of the polymer (e.g., —$C_2H_4$— monomer units of polyethylene). For example, illustrative metal loadings include those in a range of from 0.01 mol % metal to 0.6 mol % (based on monomer unit, e.g., those monomer units formed from ethylene). Preferably, providing in the reactor the supported organometallic catalyst includes providing from 0.005 mol. % to 2.0 mol. % of M based on monomer units of the polymer.

The present processes may be carried out using a variety types of reactor systems, including batch reactor systems, semi-batch reactor systems, plug flow reactor systems and continuous flow reactor systems. The volume of the reactor can be sufficient to ensure that a sufficient amount of hydrogen (e.g., moles of hydrogen) are present in the reactor relative the polymer so that the desired reduced polymer product(s) are achieved. For the various embodiments, continuous flow reactor systems can include tubular reactors, continuous stir tank reactor systems, fluid bed reactors and fixed bed reactors. In order to add heat to the reaction of the present disclosure, the reactor can include a heating jacket and/or heating coils. Heat can be provided to the reaction by providing steam to the heating jacket and/or heating coils. Alternatively, the heating jacket and/or heating coils can use a thermal fluid system (e.g., thermal oil or a water/glycol mixture) to provide the necessary heat for the reaction of the present disclosure. Other techniques for adding heat to the reaction of the present disclosure are possible.

For the various embodiments, reacting the polymer with the supported organometallic catalyst in the presence of the hydrogen gas at the predetermined temperature is for a time from 0.25 hour to 24 hours. Examples of other reaction times include those in a range of from 0.25 hour to 8 hours and 0.25 hour to 1.5 hours. Depending upon the reactivity of the catalyst, the predetermined temperature, and the pressure of hydrogen in the reactor the reaction times can be varied to achieve the desired product or product profile of the reduced polymer product having the weight average molecular weight less than the polymer.

For the various embodiments, the reduced polymer products produced according to the process of the present disclosure (e.g., hydrogenolyzed polymer products) have a weight average molecular weight less than the polymer from which they were produced. The reduced polymer products produced by the present processes include fragments of the polymer being depolymerized (e.g., the starting polymer). These fragments have weight average molecular weights that are less than that of the polymer itself. The reduced polymer products may be characterized as being a volatile product, which have relatively low weight average molecular weights and which are generally gaseous/volatile in form; an oil product, which has a more moderate weight average molecular weights and which are generally liquid in form; and a wax product, which has higher weight average molecular weights (but still less than the original polymer).

The volatile product may be characterized as having less than 9 carbons; the oil product may be characterized as having from 9 to 26 carbons; and the wax product may be characterized as having more than 26 carbons (but still less than the original polymer). The exact ranges of carbons and molecular weight ranges of the products depends upon the starting polymer as well as the specific conditions used. Similarly, the amount of each type of product depends upon the starting polymer and specific conditions. However, embodiments of the present process may be characterized as providing primarily volatile and oil products. In embodiments, the amount of wax products produced can be less than 5 weight %, less than 4 weight %, or less than 3 weight %, based on the total weight of the reduced polymer product. The present process may also be characterized as providing essentially no amount (i.e., less than 0.1 weight %) of products having a molecular weight greater than the polymer (e.g., the starting polymer). These values may be referenced with respect to a particular set of conditions, e.g., at 150° C., 2 atm $H_2$, 2 hours, 0.06 mol % metal. The reduced polymer product may be recovered and used as desired.

The present processes (and the supported organometallic catalyst used therein) may be characterized by high activities and high conversions. The activity may be quantified by a turnover frequency. The turnover frequency measured at a particular set of conditions, e.g., 150° C., 2 atm $H_2$, 2 hours, 0.06 mol % metal, may be at least 10 mol metal·mol substrate$^{-1}$·h$^{-1}$, at least 100 mol metal·mol substrate$^{-1}$·h$^{-1}$, at least 250 mol metal·mol substrate$^{-1}$·h$^{-1}$, or at least 500 mol metal·mol substrate$^{-1}$·h$^{-1}$. The conversion refers to the combined weight of dichloromethane soluble fractions and gaseous fractions recovered post-reaction as a percentage of the weight of the starting polymer. The conversion measured at a particular set of conditions, e.g., 150° C., 2 atm $H_2$, 2 hours, 0.06 mol % metal, may be at least 10%, at least 50%, at least 90%, at least 95%, at least 98%, or 100%.

It is noted that the results obtained by using the present processes are both surprising and unexpected. Although similar catalysts have been used to induce olefin polymerization and arene hydrogenation, these are mechanistically different from the hydrogenolysis/depolymerization of polymers. This fact, and the inherent unpredictability underlying organometallic chemistry, renders the remarkable activity of the present supported organometallic catalysts in the present processes truly surprising. For example, it was determined that the activity of the supported organometallic catalyst used in the Examples below to depolymerize polyethylene at 150° C., 2 atm $H_2$, 2 hours, 0.06 mol % Zr metal is about 2 orders of magnitude greater than existing catalysts in which the Zr is formally neutral and covalently bound to a metal oxide support. More specifically, the supported organometallic catalyst used in the Examples is able to depolymerize polyethylene about 100 times faster than the different catalyst, without a sulfated oxide support, used under similar conditions in Dufaud, V. R., et al., *Angew Chem Int Edit* 1998, 37 (6), 806-810. As another example, the supported organometallic catalyst used in the Example is able to depolymerize isotactic polypropylene about 180 times faster than the different catalyst used under similar conditions in Dufaud et al.

EXAMPLE

Materials and Methods

All procedures involving air- and moisture-sensitive compounds were carried out with rigorous exclusion of oxygen ($O_2$) and moisture (e.g., $H_2O$) in flame- or oven-dried Schlenk-type glassware interfaced to a high-vacuum ($10^{-5}$-$10^{-6}$ Torr) line or in an argon-filled M-Braun glovebox with a high capacity recirculator (<1 ppm $O_2$). Argon used on high-vacuum lines (Airgas, Ultra High Purity (UHP) grade) was purified by passage through MnO/vermiculite and activated Davidson 4A molecular sieve columns.

All solvents were dispensed from activated alumina/CuO columns prior to use. n-pentane (Sigma-Aldrich) was further purified by drying over Na/K alloy followed by passage through a fiberglass filter in an argon glovebox. Aluminum oxide was purchased from Nanostructured and Amorphous Materials Inc. (gamma, nanopowder 20-30 nm). Sulfuric acid (98%) was purchased from Fisher. n-hexadecane (C16) was purchased from Sigma-Aldrich and was purified by heating at 120° C. over Na for 48 hours (h), followed by degassing at room temperature (23° C.), and was further purified by three passages through a 0.22 μm PTFE syringe filter immediately prior to use. n-hexadecane-$d_{34}$ (98%+D) was purchased from Cambridge Isotope Laboratories Inc. and purified in the same manner as the C16. All components containing polymer directly contacting C16 prior to hydrogenolysis experiments (i.e., syringes, syringe filters, needles, Teflon reactor caps) were treated in the argon filled glovebox overnight prior to use. Oxygen (UHP grade) used for calcination was purchased from Airgas and used without further purification. Deuterium (Sigma-Aldrich) and hydrogen ($H_2$, UHP grade from Airgas) were purified by passage through an oxygen/moisture trap (Matheson, model MTRP-0042-XX). Zirconium (IV) chloride and neopentylmagnesium chloride (1.0 M solution in $Et_2O$) were purchased from Sigma-Aldrich and used without further purification. Tetra (neopentyl) zirconium ($ZrNp_4$) was synthesized according to the literature procedure (Davidson, P. J.; Lappert, M. F.; Pearce, R. J. *Organometal. Chem.* 1973, 57, 269-277) and purified by sublimation at 70° C. and ~106 Torr.

Polyolefins for the present examples include Engage™ 8402 polyolefin elastomer (an ethylene-octene copolymer having a density of 0.902 g/cm$^3$); Engage™ 8450 polyolefin elastomer (an ethylene-octene copolymer having a density of 0.902 g/cm$^3$); Affinity™ 1850G polyolefin plastomer (a polyethylene plastomer having a density of 0.902 g/cm$^3$); and Affinity™ GA 1900 polyolefin plastomer (a polyethylene plastomer having a density of 0.87 g/cm$^3$), all obtained from DOW®. All were used as-is in the present examples. Additional polyolefins for the present examples are acquired from high density polyethylene (HDPE) milk jugs and HDPE fruit pouch cap.

Lab-synthesized polyolefins were dried in the melt (130-165° C.) under high vacuum for 48 hours (h) before use in the hydrogenolysis reactions. Immediately prior to use, shavings of polyolefin were taken from the puck formed by the melt-drying process.

Physical and Analytical Measurements

Inductively coupled plasma atomic emission spectroscopy (ICP-AES) analysis was performed by Galbraith Laboratories Inc, Knoxville, Tennessee. 1H (500 MHZ) and $^{13}$C (125 MHz) NMR spectra of the hydrogenolysis products were obtained with a Bruker Avance III system equipped with a with a DCH Cryoprobe. 1H MAS (400 MHZ) and $^{13}$C CP-MAS (100 MHz) Solid State NMR measurements were obtained with a Bruker Avance III system equipped with a 4 mm Bruker HX probe. Rotor speed was set to 14 kHz for all spectra.

Gas chromatography mass spectrometry (GC-MS) analysis of hydrogenolysis product mixtures was carried out on an Agilent GCMSD equipped with a DB5 column (oven program: 1.) 2 minutes (min) 50° C. hold 2.) 30° C./min ramp 3.) 2 min hold at 300° C.). Split mode injection at 2 μL/injection and a 100:1 split ratio was used. For GC-MS quantification of n-hexadecane, a four-point calibration (0.1, 0.2, 0.3, 0.4 mg/mL) was carried out for each group of samples analyzed by GC-MS with a target sample concentration of ~0.2 mg/mL. Calibration standards were stored in airtight Teflon-valved glassware.

Diffuse reflectance infrared spectroscopy (DRIFTS) measurements were obtained on a Thermo 6700 infrared spectrometer equipped with a Harrick Praying Mantis DRIFTS attachment. ZnS windows were used for the DRIFTS cell. Anhydrous KBr was used as a background. The DRIFTS cell contained dry glovebox Argon (<1 ppm 02/<1 ppm $H_2O$) during all measurements. Surface area measurements were carried out with a Micromeritics 3Flex Surface Characterization Analyzer. Brunauer-Emmet-Teller (BET) surface area was measured according to S. Brunauer, P. H. Emmett, E. Teller, J. Am. Chem. Soc. 1938, 60, 309-319 using nitrogen gas adsorption analysis.

X-ray absorption near edge structure (XANES) and extended X-ray absorption fine structure (EXAFS) measurements at Zr K-edge (17998 eV) were performed at the 5 BM-D beamline of the DND-CAT at the Advanced Photon Source. A double Si (111) monochromator was used for energy selection with energy resolution of $\Delta E/E=1.4\times10^{-4}$. The X-ray energy was calibrated using a metallic Zr foil. The incident X-ray intensity was measured by a spectroscopy-grade ionization chamber (FMB-Oxford) filled with 600 He/100 $N_2$ (Torr) and was detuned to 60% of its maximum for harmonic rejection. EXAFS spectra were collected in fluorescence mode using a passivated implanted planar silicon (PIPS) detector (Canberra). The sample and the detector were positioned 45 degrees (deg) and 90 deg, respectively, to the X-ray beam direction. Energy scans were executed from 250 eV below to 550 eV above the Zr K edge which produces the EXAFS spectra.

Gel permeation chromatography (GPC) analysis was performed using a Polymer Laboratories PL-GPC 220 equipped with three PLgel 10 μm MIXED-B LS 300×7.5 mm columns and using 1,2,4-trichlorobenzene stabilized with 0.0125% butylated hydroxytoluene at 150° C. Calibration was performed using polystyrene standards (860-3,752,000 g/mol). Samples were prepared by dissolving the polymer in stabilized trichlorobenzene at 150° C. with gentle shaking overnight to yield a solution concentration of ~1.0 mg/mL, and the sample was filtered through a 0.5 μm porous stainless-steel filter prior to measurement.

AlS Synthesis

Under atmospheric conditions, sulfuric acid (2.0 M aqueous solution prepared from deionized (DI) water, 288 mL) was added to 7.0 g of aluminum oxide with stirring. The suspension was stirred for 30 min, then centrifuged (4000 rotations per minute (rpm), 5 min). The supernatant was discarded and the alumina was re-suspended in DI water and centrifuged; this step was repeated until a pH of ~6 was achieved (typically 7 washings total). The resulting solids were dried at 120° C. and ~$10^{-6}$ Torr for 18 h. The solids were then crushed via mortar and pestle and sieved to 180 mesh (80 μm). The powder was loaded into a quartz boat, placed in a tube furnace, and calcined at 550° C. under flowing $O_2$ (~2 L/min) for 3 h. The tube furnace was then interfaced to the high vacuum line and pumped down to ~$10^{-6}$ Torr for 1 h at 450° C. The furnace was cooled under vacuum and brought into an argon glovebox. The AlS (white powder, 4.83 g) was recovered and stored in a sealed container under argon.

Chemisorption of $ZrNp_4$ on AlS to form Supported Organometallic Catalyst (SOC)

In a two-sided fritted dried reaction vessel, 25 mL of pentane was condensed onto well-mixed quantities of $ZrNp_4$ (66.67 mg, 0.177 mmol) and AlS (1.000 g). The resulting slurry was stirred at 25° C. for 1 h, and then filtered. After chemisorption, the solid attained a pale yellow color. The impregnated support was collected on the frit and washed five times with ~10 mL portions of n-pentane, and then dried in vacuo for 1 h. 1H NMR was used to check for presence of remaining physiosorbed (weakly bound) $ZrNp_4$ by addition of ~10 mg of solids directly to an NMR tube with benzene-$d_6$ or toluene-$d_8$ used as the solvent. If residual organometallic was present, the catalyst was additionally washed with pentane as described above until $ZrNp_4$ was not visible in the 1H NMR. The catalyst was then stored in a sealed container at −40° C. in an argon glovebox until needed for use. Alternatively, $ZrNp_4$ and AlS were combined in a Teflon-sealed bulb, then pentane was vacuum transferred into the bulb. The mixture was stirred at 25° C. for 1 h. The pentane was removed in vacuo and the solids were dried at ~$10^{-6}$ Torr for 1 h, then stored as described above. No difference in catalytic activity was found for this alternative catalyst preparation. The SOC (AlS/$ZrNp_2$) loading was determined to be 1.40 wt. % Zr (average of two batches at 1.38 and 1.42 wt. % Zr) by ICP-AES. The catalyst BET surface area was 184 m$^2$/g by $N_2$ physisorption, so that the Zr coverage is, 0.50 Zr/nm$^2$.

Synthesis of AlS/$ZrH_2$, AlS/$ZrD_2$ and pAlS/$ZrH_2$ (Pentane-treated AlS/$ZrH_2$)

Synthesis of AlS/$ZrH_2$. In the glovebox, AlS/$ZrNp_2$ (200 mg) was placed in a 75 mL glass pressure reactor. The reactor was sealed, interfaced with a high pressure/high vacuum line, evacuated, then charged with 1 atmosphere (atm, 101.325 kPa) $H_2$. The reactor was heated to 150° C. for 5 min, then evacuated. The catalyst color changed from pale yellow to colorless. This cycle was repeated once more. The AlS/ZrH$_2$ was then used as needed for further reactions or measurements. AlS/ZrD$_2$ was synthesized in an analogous fashion to AlS/ZrH$_2$, using D$_2$ in place of H$_2$. To synthesize pAlS/ZrH$_2$, pentane (~0.5 mL) was vacuum transferred into a 75 mL pressure reactor containing AlS/ZrNp$_2$ (200 mg) on a high pressure/high vacuum line. The reactor was heated at 150° C. for 5 min. In the first 30 s of heating, a color change from colorless to pale yellow was observed. Catalysts were stored at −40° C. in an argon glovebox until needed.

General Hexadecane Hydrogenolysis Procedure with AlS/ZrNp$_2$:

In the glovebox, C16 was passed through a 0.22 μm PTFE syringe filter directly into a heavy-walled glass pressure reactor containing a 10 mm ovoid stir bar. The AlS/ZrNp$_2$ was added to the reactor and it was sealed with a threaded Teflon cap with a National Pipe Thread Taper (NPT) valve installed. The vessel was carefully removed from the glovebox and interfaced with a high pressure/high vacuum line. The reactor was degassed at room temperature for 90 seconds (s), then charged to the needed pressure of H$_2$. The reactor was placed in an oil bath set to the desired temperature and stirring was initiated at about 500 rpm. Once the oil bath thermocouple reached reaction temperature, the time interval was started. At the end of the time interval, the reactor was removed from the oil bath, then cooled via water bath to room temperature. Headspace samples were taken, if needed, at this point. The reactor was vented through the NPT valve and opened to air. Approximately 5 mL dichloromethane (DCM) was used to wash the Teflon cap and the interior of the NPT valve. These washings were added to the reactor. The washings were transferred to a syringe equipped with a 0.22 μm PTFE filter. The reactor was washed 4 times (×) with ~10 mL portions of clean DCM, with each washing being added to the syringe. The washings were passed through the filter directly into a 100 mL volumetric flask. The filter was washed 4× with ~5 mL portions of clean DCM, with washings being added to the volumetric flask. Pipettes used to transfer DCM solutions were also washed with clean DCM and added to the volumetric flask. The solution was diluted to the calibration mark, then diluted further using standard analytical techniques to ~0.2 mg/mL.

General Polyolefin Hydrogenolysis Procedure:

In the glovebox, AlS/ZrNp$_2$ and the desired amount of polyolefin sample were loaded into a heavy-walled glass pressure reactor containing a 10 mm ovoid stir bar, typically with ~15% mass loading of SOC. Lab-made polyolefin samples were prepared by shaving from a larger puck of pre-melted stock. DOW® polyolefin samples were used as-is. Postconsumer polyolefin samples were finely divided using either a cheese grater or scissors. The reactor was sealed with a threaded Teflon cap with an NPT valve installed. The vessel was carefully removed from the glovebox and interfaced with a high pressure/high vacuum line. The reactor was degassed at room temperature for 90 s, then charged to 2 atm H$_2$. The reactor was placed in an oil bath set to the desired temperature (90-200° C.).

Once the polyolefin melted and contacted the catalyst in the melt, the time interval was started. Stirring was typically set to 300 rpm initially, then increased to ~800 rpm after a sufficient decrease in polyolefin viscosity. At the end of the time interval, the reactor was removed from the oil bath, then air-cooled to room temperature. If needed, headspace samples were taken at this point. Headspace samples were taken by expansion of the reactor contents into an evacuated 500 mL Teflon-valved glass bulb. Individual samples for analysis were withdrawn via septum and gastight headspace syringe (50 μL). The reactor was vented through the NPT valve and opened to air. Approx. 5 mL DCM was used to wash the Teflon cap and the interior of the NPT valve. These washings were added to the reactor. Solids were suspended in the DCM washings then filtered to isolate the solids. The reactor was washed enough times to remove all residue. The solids were washed ~3× with 5 mL portions of DCM, then dried at ~1 Torr (133 pascal) overnight (solid fraction). The DCM was removed from the filtrate (DCM extract fraction) and the resulting liquid was dried overnight at ~1 Torr (133 pascal).

Results for AlS/ZrNp$_2$

The results seen in Table 1 show a full conversion of the C16 using the above discussed general hexadecane hydrogenolysis procedure with AlS/ZrNp$_2$. For the below data, experiment "a" in Table 1 was conducted at 2 atm of H$_2$ in a 500 mL reactor with 3.0 g C16 and 200 mg AlS/ZrNp$_2$ (1.40 wt. wt % Zr). Experiment "b" in Table 1 was conducted at 2.5 atm of H$_2$ in a 350 mL reactor with 1.483 g C16 and 178 mg AlS/ZrNp$_2$ (0.17 wt. wt % Zr). The average carbon chain length was estimated by 1H NMR with the assumption of only linear chains being present. As seen in Table 1, there was a 100 percent conversion of the C16.

TABLE 1

| Temperature (° C.) | $H_2$ Pressure (atm) | Reaction time (min) | SOC loading (Zr mol %) | Hexadecane conversion (%) |
|---|---|---|---|---|
| 150 | 2.0[a] | 270 | 0.23 | 100 (6.4 C avg)[b] |
| 150 | 2.5[c] | 18 | 0.42 | 100 (7.5 C avg.)[b] |

Table 2 provides variable-pressure C16 hydrogenolysis reaction data. The results seen in Table 2 show that there is an absence of an H$_2$ pressure dependence (and by extension H$_2$ concentration), which is consistent with zero-order kinetics in H$_2$. For the experiments of Table 2, there was 2.5 wt % of the AlS/ZrNp$_2$ in the reactor (1.40 wt. wt % Zr). For experiment "a" in Table 2, there were seven (7) equivalents of H$_2$ with respect to C16.

TABLE 2

C16 hydrogenolysis conversion as a function of $H_2$ pressure

| Temperature (° C.) | $H_2$ Pressure (atm) | Reaction time (min) | SOC loading (Zr mol %) | Hexadecane conversion (%) |
|---|---|---|---|---|
| 120 | 0.5[a] | 15 | 0.17 | 11.5 |
| 120 | 1.0 | 15 | 0.17 | 11.2 |
| 120 | 2.0 | 15 | 0.17 | 11.8 |
| 120 | 4.0 | 15 | 0.17 | 12.0 |

Table 3 provides variable-catalyst loading C16 hydrogenolysis reaction data for AlS/ZrNp$_2$ (1.40 wt. wt % Zr, 0.6-5.44 wt % catalyst in the reactor). The data shows a linear relationship ($R^2$=0.98451) between conversion and catalyst loading, which suggests a first order kinetics with respect to the catalyst concentration.

TABLE 3

C16 hydrogenolysis conversion as a function of catalyst loading

| Temperature (° C.) | $H_2$ Pressure (atm) | Reaction time (min) | SOC loading (Zr mol %) | Hexadecane conversion (%) | Activity (mol C16/mol Zr · h) |
|---|---|---|---|---|---|
| 120 | 2.0 | 15 | 0.37 | 28.2 | 304 |
| 120 | 2.0 | 15 | 0.27 | 17.0 | 256 |
| 120 | 2.0 | 15 | 0.22 | 14.8 | 268 |
| 120 | 2.0 | 15 | 0.17 | 11.8 | 274 |
| 120 | 2.0 | 15 | 0.09 | 1.3 | 63 |
| 120 | 2.0 | 15 | 0.04 | 0.5 | 444 |

Table 4 provides data on the C16 hydrogenolysis conversion as a function of time for AlS/$ZrNp_2$ (1.40 wt. wt % Zr 2.5 wt % SOC in the reactor). The data demonstrates a linear relationship ($R^2$=0.9346) between time and conversion of the C16, which is suggest a pseudo-zero order conditions employed in kinetic experiments.

TABLE 4

C16 hydrogenolysis conversion as a function of time

| Temperature (° C.) | $H_2$ Pressure (atm) | Reaction time (min) | SOC loading (Zr mol %) | Hexadecane conversion (%) |
|---|---|---|---|---|
| 90 | 2.0 | 15 | 0.17 | 3.1 |
| 90 | 2.0 | 30 | 0.17 | 5.1 |
| 90 | 2.0 | 45 | 0.17 | 7.5 |
| 90 | 2.0 | 60 | 0.17 | 12.3 |
| 90 | 2.0 | 75 | 0.17 | 11.1 |
| 90 | 2.0 | 90 | 0.17 | 14.9 |

Table 5 provides data on temperature variation in the C16 hydrogenolysis with AlS/$ZrNp_2$ (1.40 wt. wt % Zr, 2.5 wt % catalyst in the reactor). The data demonstrates a linear relationship ($R^2$=0.99924) between temperature and conversion of the C16, which suggests a first order kinetics with respect to the reaction temperature.

TABLE 5

C16 hydrogenolysis conversion as a function of temperature

| Temperature (° C.) | $H_2$ Pressure (atm) | Reaction time (min) | SOC loading (Zr mol %) | Hexadecane conversion (%) |
|---|---|---|---|---|
| 90 | 2.0 | 15 | 0.17 | 3.1 |
| 110 | 2.0 | 15 | 0.17 | 8.8 |
| 120 | 2.0 | 15 | 0.17 | 11.8 |
| 130 | 2.0 | 15 | 0.17 | 15 |
| 150 | 2.0 | 15 | 0.17 | 20.4 |

Figure 2:
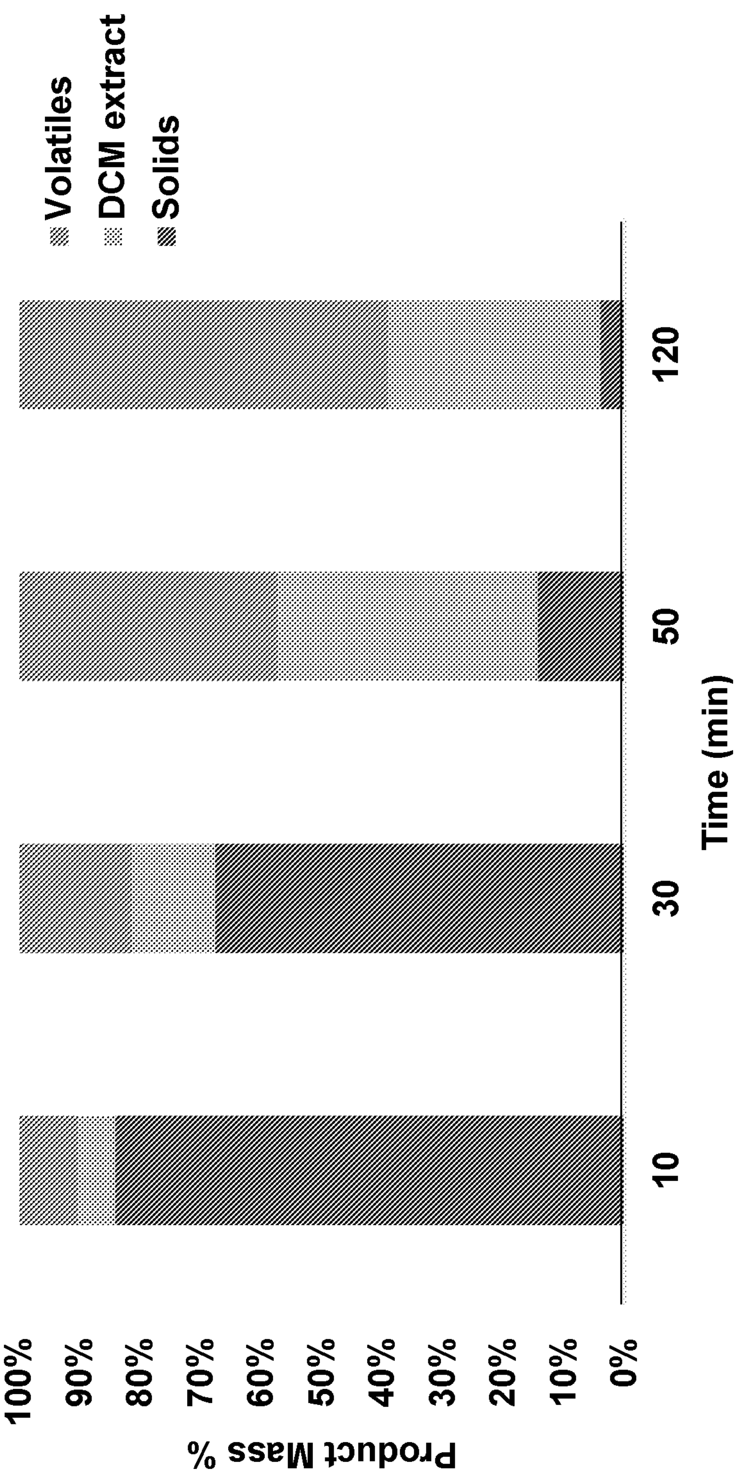
FIG. 2 shows the mass percent of the volatile, DCM extract and solids product for the reduced polymer product of Table 6.

Table 6 provides data on the conversion of pristine, lab-synthesized polyethylene homopolymer ($M_n$~9 kg·mol$^{-1}$) to gaseous and DCM-soluble hydrocarbons as a function of time with AlS/$ZrNp_2$ (1.40 wt % Zr, 12.5 wt % catalyst in the reactor). FIG. 2 shows the mass percent of the volatiles, DCM extract and solids products for the reduced polymer products of Table 6.

TABLE 6

Lab-made polyethylene hydrogenolysis conversion as a function of time

| Temperature (° C.) | $H_2$ Pressure (atm) | Reaction time (min) | Polymer Mass (g) | Catalyst mass (g) | SOC loading (Zr mol %) | Conversion to gaseous/ DCM-soluble hydrocarbons (%) |
|---|---|---|---|---|---|---|
| 150 | 2.0 | 10 | 1.453 | 0.216 | 0.06 | 16 |
| 150 | 2.0 | 30 | 1.514 | 0.216 | 0.06 | 32 |
| 150 | 2.0 | 50 | 1.444 | 0.214 | 0.06 | 86 |
| 150 | 2.0 | 120 | 1.514 | 0.216 | 0.06 | 96 |

Figures 3, 4:
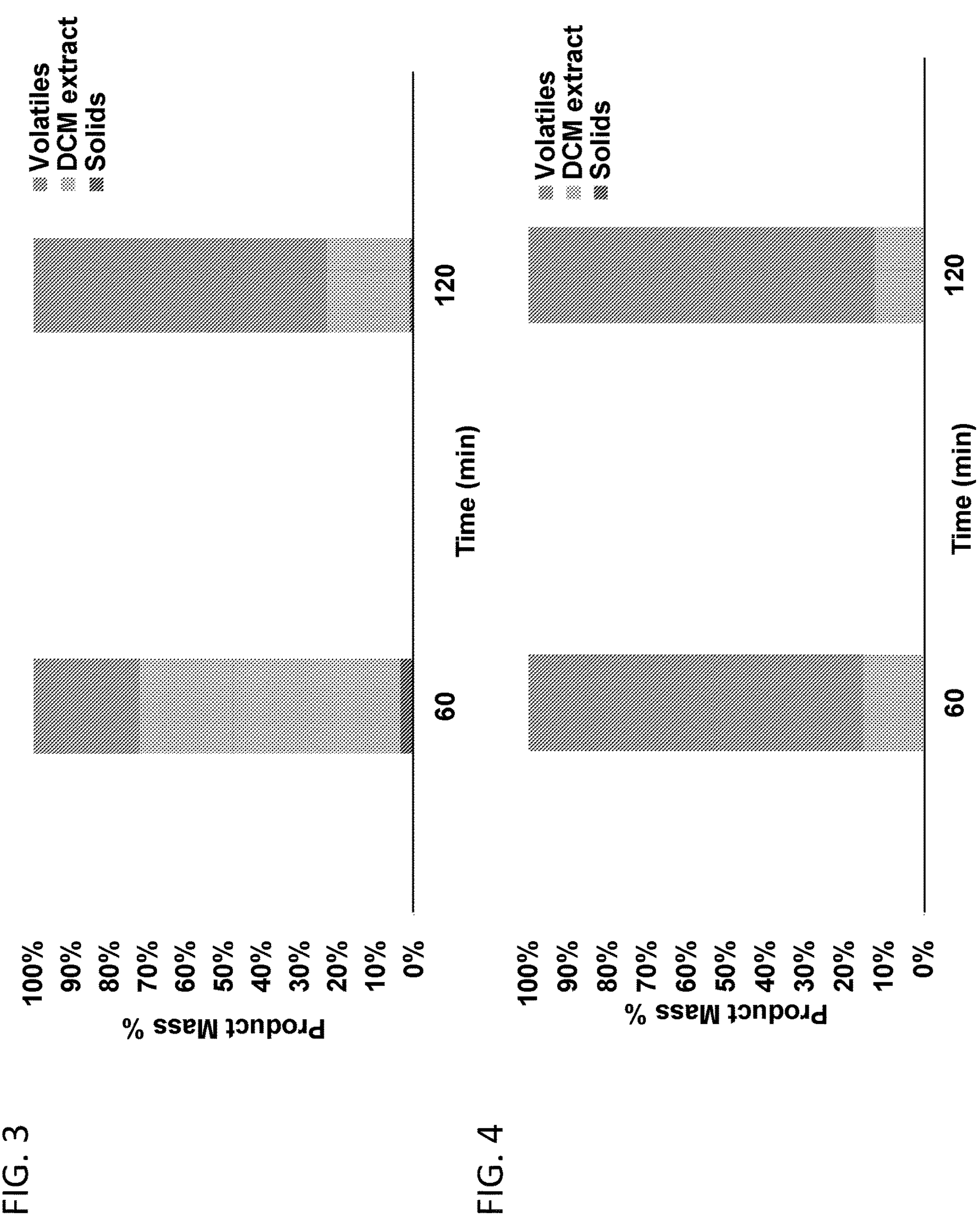
FIG. 3 shows the mass percent of the volatile, DCM extract and solids product for the reduced polymer product of Table 7.
FIG. 4 shows the mass percent of the volatile, DCM extract and solids product for the reduced polymer product of Table 8.

Table 7 provides data on the conversion of pristine, lab-synthesized isotactic polypropylene homopolymer ($M_n$~36 kg·mol$^{-1}$) to gaseous and DCM-soluble hydrocarbons as a function of time with AlS/$ZrNp_2$ (1.40 wt % Zr, 17 wt % catalyst in the reactor). FIG. 3 shows the mass percent of the volatiles, DCM extract and solids products for the reduced polymer products of Table 7.

TABLE 7

Lab-made isotactic polypropylene hydrogenolysis conversion as a function of time

| Temperature (° C.) | $H_2$ Pressure (atm) | Reaction time (min) | Polymer mass (g) | Catalyst Mass (g) | SOC loading (Zr mol %) | Conversion to gaseous/ DCM-soluble hydrocarbons (%) |
|---|---|---|---|---|---|---|
| 190 | 2.0 | 60 | 1.097 | 0.209 | 0.13 | 96 |
| 190 | 2.0 | 120 | 1.026 | 0.210 | 0.13 | 99 |

Table 8 provides data on the conversion of pristine, lab-synthesized polyethylene-co-1-octene (2.5% 1-octene incorporation, $M_n$~7 kg·mol$^{-1}$) to gaseous and DCM-soluble hydrocarbons as a function of time with AlS/$ZrNp_2$ (1.40 wt % Zr, 13 wt % catalyst in the reactor). FIG. 4 shows the mass percent of volatiles, DCM extract and solids products for the reduced polymer products of Table 8.

TABLE 8

Lab-made polyethylene-co-1-octene hydrogenolysis conversion as a function of time

| Temperature (° C.) | $H_2$ Pressure (atm) | Reaction time (min) | Polymer mass (g) | Catalyst Mass (g) | SOC loading (Zr mol %) | Conversion to gaseous/ DCM-soluble hydrocarbons (%) |
|---|---|---|---|---|---|---|
| 190 | 2.0 | 60 | 1.139 | 0.177 | 0.07 | >99 |
| 190 | 2.0 | 120 | 1.157 | 0.179 | 0.07 | >99 |

Discussion of Results for AlS/$ZrNp_2$

A $d^0$ formally cationic Zr(IV) hydrocarbyl supported on an acidic metal oxide support is observed to catalyze the most rapid hydrogenolysis of polyolefins and alkanes currently known under the reported reaction conditions. In comparison to formally neutrally charged Zr catalysts supported on weakly acidic surfaces, this system shows at least a two orders of magnitude enhancement in activity. Kinetic experiments show that the reaction is zero order in both hexadecane and $H_2$ and is first order in catalyst. DRIFTS and SSNMR both provide evidence for the presence of a Zr hydride as the active species.

The AlS/$ZrNp_2$ SOC used in the alkane (C16) and polyolefin hydrogenolysis experiments described above is a formally cationic (positively charged) Zr alkyl complex adsorbed on/activated by an acidic metal oxide support (e.g., an extremely Brønsted acidic sulfated alumina support, FIG. 1B). In contrast, previous Zr alkane and polyolefin hydrogenolysis catalysts were formally neutrally charged (i.e., uncharged) Zr complexes covalently bound to weakly Brønsted acidic supports (FIG. 1A). Despite their similar bulk stoichiometric compositions, the present cationic, noncovalently bound Zr alkyl complexes significantly outperform previous catalysts and can completely convert polyethylene and other polyolefins to volatile products (<$C_9$), oil products ($C_9$-$C_{26}$), and trace amounts of wax products ($C_{26}$-$C_{60}$~3%) after only 2 h at 150° C. under 2 atm $H_2$ pressure, and 0.06 mol % Zr loading (based on —$C_2H_4$— monomer units) on the acidic metal oxide support. The organometallic complex precatalyst used in the experiments above, tetrakis(neopentyl)zirconium, is among a series of electron deficient group 4 metal hydrocarbyls and hydrides that can be immobilized on acidic metal oxide supports such as sulfated metal oxides (e.g., sulfated alumina). Although similar catalysts have been shown to be active for olefin polymerization and arene hydrogenation, it was completely unexpected that they would activate saturated hydrocarbons and polyolefins to achieve high yields of depolymerization/hydrogenolysis products under relatively mild conditions. In fact, as demonstrated above, the example catalyst shown in FIG. 1B is extremely active for alkane hydrogenolysis and mediates complete conversion of polyethylene, isotactic polypropylene, and polyethylene-co-1-octene to light hydrocarbons and waxes in less than 2 hours, using low catalyst loadings (0.06-0.13 mol % Zr) and mild conditions (150-190° C., 2 atm $H_2$).

Chemisorption of $HfNp_4$ on AlS to Form SOC

Tetra(neopentyl)hafnium ($HfNp_4$) was synthesized according to the literature procedure (Davidson, P. J.; Lappert, M. F.; Pearce, R. *J. Organometal. Chem.* 1973, 57, 269-277) and purified by sublimation at 80° C. and ~$10^{-6}$ Torr. In a two-sided fritted dried reaction vessel, 25 mL of pentane was condensed onto well-mixed quantities of $HfNp_4$ (84.0 mg, 0.181 mmol) and AlS (1.000 g). The resulting suspension was stirred at 25° C. for 1 h, then filtered. After chemisorption, the solid remained white. The impregnated support was collected on the frit and washed five times with ~10 mL portions of n-pentane, and then dried in vacuo for 1 h. The catalyst was then stored in a sealed container at 25° C. in an argon glovebox until needed for use. The SOC (AlS/$HfNp_2$) loading was determined to be 3.28 wt. % Hf by ICP-AES.

General C16 Hydrogenolysis Procedure with AlS/$HfNp_2$

In the glovebox, C16 was passed through a 0.22 μm PTFE syringe filter directly into a heavy-walled glass pressure reactor containing the desired amount of the SOC. The reactor was sealed with a threaded Teflon cap with an NPT valve installed. The vessel was then degassed at room temperature for 90 seconds and refilled with 2 atm $H_2$. The reactor was placed in an oil bath set to 150° C. and stirring was initiated at about 200 rpm. Once the oil bath thermocouple reached 147° C., the time interval was started. The time for all the C16 disappear visually was recorded. Headspace and condensed samples were taken and characterized by GC-Fid and GC-MS respectively.

Table 9 provides variable-pressure C16 hydrogenolysis reaction data. The results seen in Table 9 show that there is an absence of an $H_2$ pressure dependence (and by extension $H_2$ concentration), which is consistent with zero-order kinetics in $H_2$. For the experiments of Table 9, there was 4.2 wt % of the AlS/$HfNp_2$ SOC in the reactor (0.14 wt % Hf).

TABLE 9

C16 hydrogenolysis conversion as a function of $H_2$ pressure; Hf catalyst

| Temperature (° C.) | $H_2$ Pressure (ATM) | Reaction time (min) | SOC Loading (Hf mol %) | Hexadecane conversion (%) |
|---|---|---|---|---|
| 180 | 1.0 | 15 | 0.13 | 11.3 |
| 180 | 1.5 | 15 | 0.14 | 13.8 |
| 180 | 2.0 | 15 | 0.14 | 12.7 |

Table 10 provides variable-catalyst loading C16 hydrogenolysis reaction data for AlS/$HfNp_2$ (3.28 wt % Hf). The data shows a linear relationship ($R^2$=0.9889) between conversion and catalyst loading, which suggests a first order kinetics with respect to the SOC concentration.

TABLE 10

| C16 hydrogenolysis conversion as a function of Hf catalyst loading | | | | |
|---|---|---|---|---|
| Temperature (° C.) | $H_2$ Pressure (ATM) | Reaction time (min) | SOC Loading (Hf mol %) | Hexadecane conversion (%) |
| 180 | 2.0 | 15 | 0.071 | 4.49 |
| 180 | 2.0 | 15 | 0.15 | 12.7 |
| 180 | 2.0 | 15 | 0.22 | 21.9 |
| 180 | 2.0 | 15 | 0.31 | 36.6 |

Table 11 provides data on temperature variation in the C16 hydrogenolysis with AlS/HfNp$_2$ (3.28 wt % Hf). The data demonstrates a linear relationship ($R^2$=0.8404) between temperature and conversion of the C16, which suggests a first order kinetics with respect to the reaction temperature.

TABLE 11

| C16 hydrogenolysis conversion as a function of reaction temperature; Hf catalyst | | | | |
|---|---|---|---|---|
| Temperature (° C.) | $H_2$ Pressure (ATM) | Reaction time (min) | SOC Loading (Hf mol %) | Hexadecane conversion (%) |
| 140 | 2.0 | 15 | 0.15 | 1.02 |
| 160 | 2.0 | 15 | 0.15 | 6.17 |
| 180 | 2.0 | 15 | 0.15 | 12.7 |
| 190 | 2.0 | 15 | 0.15 | 11.4 |
| 200 | 2.0 | 15 | 0.14 | 15.4 |
| 210 | 2.0 | 15 | 0.14 | 28.0 |

Table 12 provides selected data from polyethylene (Engage™ 8402) hydrogenolysis reactions in Parr 25 mL autoclave using AlS/HfNp$_2$ (3.28 wt % Hf) and stirring was initiated at about 1500 rpm.

TABLE 12

| C16 hydrogenolysis conversion as a function of $H_2$ pressure and reaction time; Hf catalyst | | | | | | | | |
|---|---|---|---|---|---|---|---|---|
| | $H_2$ | | | | Product Distribution | | | Average Chain |
| Temperature (° C.) | Pressure (atm) | Reaction Time (h) | Polyethylene Mass (mg) | SOC Mass (mg) | Volatile (mg) | Oil (mg) | Wax (mg) | Length of Solid |
| 200 | 18 | 1 | 1014.9 | 116.9 | 706.2 | 180.1 | 128.6 | — |
| 200 | 18 | 1 | 1009.7 | 50.4 | 602.0 | 377.7 | 30.1 | — |
| 200 | 18 | 1 | 996.0 | 24.9 | 251.5 | 246.6 | 497.9 | — |
| 200 | 11 | 2 | 2030.0 | 99.9 | 177.4 | 7.7 | 1844.9 | 28 |
| 250 | 15.5 | 2 | 2027.3 | 52.3 | 10.3 | 9.2 | 2007.8 | 45 |
| 250 | 18 | 1 | 2027.8 | 50.2 | 67.3 | 48.4 | 1912.1 | 39 |

Discussion of Results for AlS/HfNp$_2$

The AlS/HfNp$_2$ SOC is a structural analogue of the AlS/ZrNp$_2$ SOC, in which the metal has been replaced by Hf. As seen in the above data, the AlS/HfNp$_2$ SOC can catalyze rapid hydrogenolysis of polyolefins and alkanes. While the rate of hydrogenolysis is lower than that of the Zr catalyst under the same conditions, the Hf system is observed to have greater thermal stability.

Chemisorption of Ta(CH$^t$Bu)Np$_3$ on AlS to Form SOC

Ta(CH$^t$Bu)Np$_3$ was synthesized according to the literature procedure (Schrock, R. R.; Fellmann, J. D. *J. Am. Chem. Soc.,* 1978, 100, 3359). In a dry two-sided fritted dried reaction vessel, 20 mL of pentane was vacuum transferred into a mixture of Ta(CH$^t$Bu)Np$_3$ (100 mg, 0.215 mmol) and AlS (1.20 g). The resulting suspension was stirred at 25° C. for 2 h, and then filtered. After chemisorption, the solid attains a pale-yellow color. The impregnated support was collected on the frit and washed five times with ~10 mL portions of pentane, and then dried in vacuo for 1 h. The catalyst was stored at −40° C. in an argon glovebox until needed. The AlS/Ta(CH$^t$Bu)Np SOC loading was 2.75 wt. % Ta as determined by ICP-AES.

Chemisorption of TiNp$_4$ on AlS to Form SOC

TiNp$_4$ was synthesized according to the literature procedure (Cheon, J.; Rogers, D. M.; Girolami G. S. *J. Am. Chem. Soc.,* 1997, 119, 6804). In a dry two-sided fritted dried reaction vessel, 20 mL of pentane was vacuum transferred into a mixture of TiNp$_4$ (53 mg, 0.159 mmol) and AlS (0.90 g). The resulting suspension was stirred at 25° C. for 1 h, and then filtered. After chemisorption, the solid attains a pale-yellow color. The impregnated support was collected on the frit and washed five times with ~10 mL portions of pentane, and then dried in vacuo for 1 h. The catalyst was stored at −40° C. in an argon glovebox until needed. The AlS/TiNp$_2$ SOC loading was approximately 0.7 wt. % Ti.

Chemisorption of NbF$_2$Np$_3$ on AlS to Form SOC

NbF$_2$Np$_3$ was synthesized according to the literature procedure (Schrock, R. R.; Fellmann, J. D. *J. Am. Chem. Soc.,* 1978, 100, 3359). In a dry two-sided fritted dried reaction vessel, 20 mL of pentane was vacuum transferred into a mixture of NbF$_2$Np$_3$ (100 mg, 0.215 mmol) and AlS (1.20 g). The resulting suspension was stirred at 25° C. for 2 h, and then filtered. The impregnated support was collected on the frit and washed five times with ~10 mL portions of pentane, and then dried in vacuo for 1 h. The catalyst was stored at −40° C. in an argon glovebox until needed. The AlS/NbF$_2$Np SOC loading was approximately 1.4 wt. % Nb.

Chemisorption of Nb(CH$^t$Bu)Np$_3$ on AlS to form SOC

NbCl$_2$Np$_3$ was synthesized according to the literature procedure (Schrock, R. R.; Fellmann, J. D. *J. Am. Chem. Soc.,* 1978, 100, 3359). To a 50 mL Schlenk flask, 99 mg NbCl$_2$Np$_3$ (0.26 mmol) was loaded with 10 mL pentane and a stir bar. The NbCl$_2$Np$_3$ solution was cooled in a dry ice-acetone bath for 10 min, before the slow addition of LiNp (46 mg, 0.58 mmol) pentane solution via cannula transfer. The resulting suspension was stirred for another 10 min and then warmed up to 0° C. in an ice bath. The color of the suspension turned wine-red from orange yellow. To a dry two-sided fritted dried reaction vessel, AlS (1.20 g) was loaded and then cooled in an ice-water bath. The above mentioned wine-red suspension was added to the AlS support via cannula filtration. The resulting suspension was stirred at 0° C. for 1 h, and then filtered. After chemisorption, the solid attains a pale-yellow color. The impregnated support was collected on the frit and washed five times with ~10 mL portions of pentane, and then dried in vacuo for 1 h. The catalyst was stored at −40° C. in an argon glovebox until needed. The SOC (AlS/Nb(CH$^t$Bu)Np) loading was approximately 1.4 wt. % Nb.

Chemisorption of W(C$^t$Bu)$Np_3$ on AlS to Form SOC

W(C$^t$Bu)$Np_3$ was synthesized according to the literature procedure (Dewan, J. C.; Schrock, R. R. *J. Am. Chem. Soc.,* 1978, 100, 6774). In a dry two-sided fritted dried reaction vessel, a mixture of W(C$^t$Bu)$Np_3$ (105 mg, 0.225 mmol) and AlS (1.23 g) was heated in a 66° C. oil bath for 5 h. 20 mL of pentane was vacuum transferred into the resulting mixture and then filtered. After chemisorption, the solid attains a pale-brown color. The impregnated support was collected on the frit and washed five times with ~10 mL portions of pentane, and then dried in vacuo for 1 h. The SOC was stored at −40° C. in an argon glovebox until needed. The SOC (AlS/W(C$^t$Bu)Np) loading was approximately 2.8 wt % W.

Chemisorption of Mo(C$^t$Bu)$Np_3$ on AlS to Form SOC

Mo(C$^t$Bu)$Np_3$ was synthesized according to the literature procedure (McCullough, L. G.; Schrock, R. R.; Dewan, J. C.; Murdzek. J. C. *J. Am. Chem. Soc.,* 1985, 107, 5987). In a dry two-sided fritted dried reaction vessel, a mixture of Mo(C$^t$Bu)$Np_3$ (52 mg, 0.137 mmol) and AlS (0.75 g) was heated in a 50° C. oil bath for 2 h. 10 mL of pentane was vacuum transferred into the resulting mixture and then filtered. After chemisorption, the solid attains a pale-brown color. The impregnated support was collected on the frit and washed five times with ~10 mL portions of pentane, and then dried in vacuo for 1 h. The catalyst was stored at −40° C. in an argon glovebox until needed. The SOC (AlS/Mo(C$^t$Bu)Np) loading was approximately 1.4 wt % W.

General C16 Hydrogenolysis Procedure for Initial SOC Screening

In the glovebox, C16 (typically ~1.5 g) was passed through a 0.22 μm PTFE syringe filter directly into a heavy-walled glass pressure reactor (350 mL volume) containing the desired amount of catalyst (typically ~170 mg). The reactor was sealed with a threaded Teflon cap with an NPT valve installed. The vessel was then degassed at room temperature for 90 s and refilled with 2 atm $H_2$. The reactor was placed in an oil bath set to 150° C. Once the oil bath thermocouple reached 147° C., the time interval was started. The time for all the C16 evaporated was recorded. Headspace and condensed samples were taken and characterized by GC-Fid and GC-MS respectively.

General Polyolefin Hydrogenolysis Procedure for AlS/Ta(CH$^t$Bu)Np

In the glovebox, AlS/Ta(CH$^t$Bu)Np and the desired amount of polyolefin sample were loaded into a heavy-walled glass pressure reactor (350 mL volume) with ~15% mass loading of the SOC. The reactor was sealed with a threaded Teflon cap with an NPT valve installed. The reactor was degassed and refilled with 2 atm $H_2$. The reactor was placed in an oil bath set to the desired temperature. Once the polyolefin melted and contacted the catalyst, the time interval was started. Stirring was typically set to 300 rpm initially, then increased to 600 rpm after sufficient decrease in polyolefin viscosity. At the end of the time interval, the vessel was removed from the oil bath, then air-cooled to room temperature. If needed, headspace samples were taken at this point. The reactor was vented through the NPT valve and opened to air. Approximately 5 mL DCM was used to wash the Teflon cap and the interior of the NPT valve. These washings were added to the reactor. Solids were suspended in the DCM washings then filtered for collection. The reactor was washed enough times to remove all the residue. The solids collected on the frit were washed ~3× with 5 mL portions of DCM, then dried at ~100 mTorr overnight (wax product). The DCM was removed from the filtrate (DCM extract fraction) and the resulting liquid was dried overnight at ~100 mTorr.

TABLE 13

Hydrogenolysis data for lab polyethylene at different temperatures carried out in a glass reactor

| Temperature (° C.) | $H_2$ Pressure (atm) | Reaction time (min) | SOC Loading (mg) | Mass of PE (mg) |
|---|---|---|---|---|
| 160 | 2 | 60 | 76 | 501 |
| 180 | 2 | 60 | 73 | 515 |
| 200 | 2 | 60 | 75 | 505 |
| 220 | 2 | 60 | 77 | 517 |
| 250 | 2 | 60 | 79 | 502 |

Figure 5:
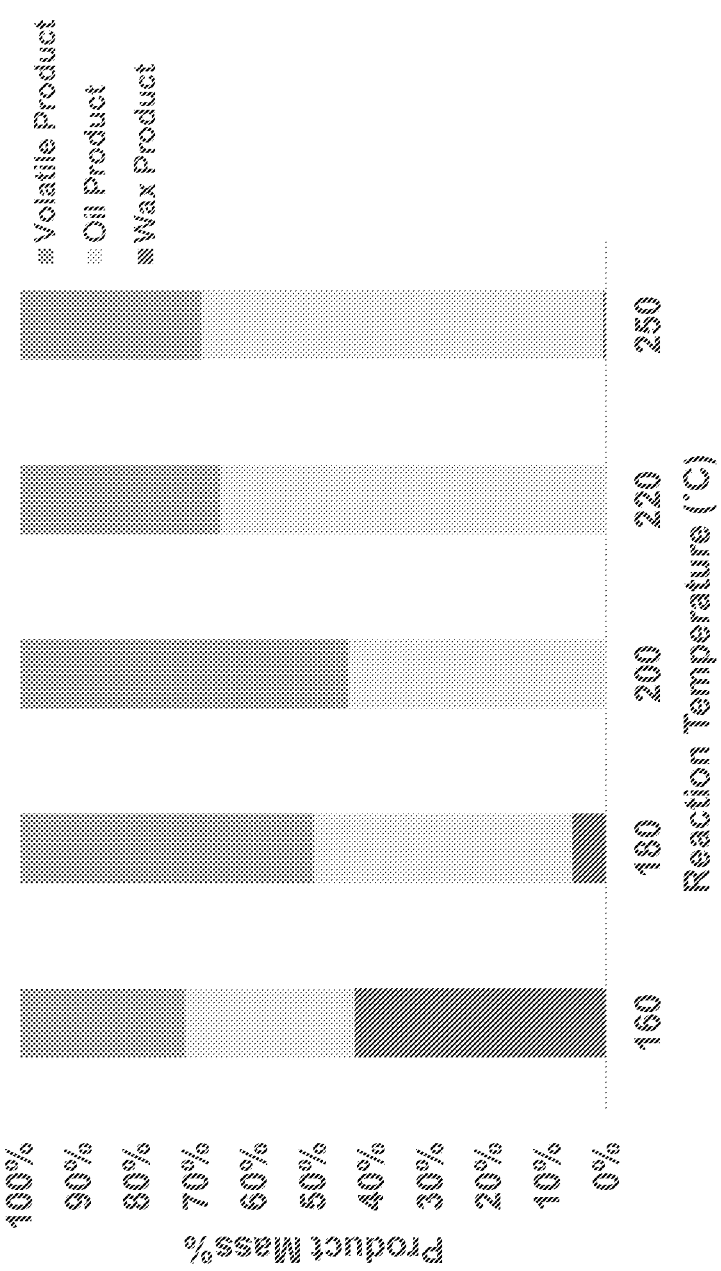
FIG. 5 shows the mass percent of the volatile product, the oil product and the wax product for the reduced polymer product of Table 13.

FIG. 5 shows the mass percent of the volatile product, the oil product and the wax product for the reduced polymer products of Table 13.

TABLE 14

Hydrogenolysis data of lab-made polyethylene catalyzed by AlS/Ta(CH$^t$Bu)Np carried out in a glass reactor

| Temperature (° C.) | $H_2$ Pressure (atm) | Reaction time (min) | SOC Loading (mg) | Mass of PE (mg) |
|---|---|---|---|---|
| 200 | 2 | 10 | 77 | 500 |
| 200 | 2 | 20 | 77 | 510 |
| 200 | 2 | 30 | 71 | 502 |
| 200 | 2 | 60 | 77 | 517 |
| 200 | 2 | 120 | 78 | 523 |

Figure 6:
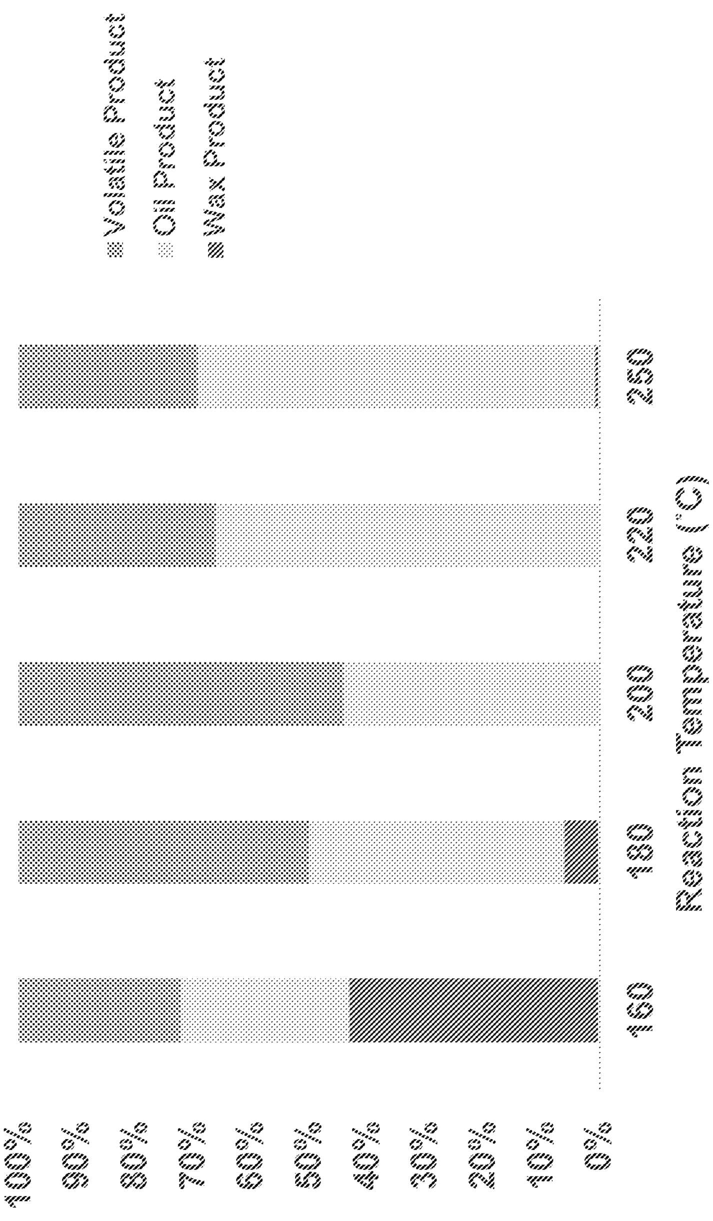
FIG. 6 shows the mass percent of the volatile product, the oil product and the wax product for the reduced polymer product of Table 14.

FIG. 6 shows the mass percent of the volatile product, the oil product and the wax product for the reduced polymer products of Table 14.

C16 Hydrogenolysis

In the glovebox, 300 mg AlS/Ta(CH$^t$Bu)Np were loaded into a heavy-walled glass pressure reactor (350 mL volume). The reactor was sealed with a threaded Teflon cap with an NPT valve installed. The reactor was degassed and refilled with 2 atm $H_2$, then placed in a 200° C. oil bath for 5 min. The reactor was degassed and refilled with 1 atm C16/$H_2$ (1:1 ratio), then placed in a 200° C. oil bath for 4 h. Headspace sample was measured by GC-Fid. The results are shown in Table 15. Table 15 provides the time interval recorded to evaporate all C16 by hydrogenolysis according to the above process.

TABLE 15

C16 hydrogenolysis conversion time as a function of catalyst

| SOC | AlS/ $TiNp_2$ | AlS/ $NbF_2Np$ | AlS/ Nb(CH$^t$Bu)Np | AlS/ Ta(CH$^t$Bu)Np | AlS/ Mo(C$^t$Bu)Np | AlS/ W(C$^t$Bu)Np |
|---|---|---|---|---|---|---|
| Reaction time (min) | 120 | 435 | 151 | 125 | 600 | >720 |

CONCLUSIONS

On chemisorption of group V and VI hydrocarbyl precursors on acidic sulfated alumina (AlS), single-site cationic group V & VI organometallic centers are produced which were super active in polyolefin hydrogenolysis. The ethane hydrogenolysis experiment reveals a new C—C bond activation mechanism for Group V metals. The heavier metal catalysts exhibit higher thermal stability than the corresponding single-site Zr catalysts.

Polyolefin Hydrogenolysis

General High Pressure Hydrogenolysis Procedure with AlS/$ZrNp_2$

In the glovebox, catalyst (typically $10^{-3}$ wt %) and polyolefin was added to a 25-100 mL Parr reactor with equipped with magnetically coupled overhead stirring and a PTFE reactor liner. The reactor was sealed, removed from the glovebox and interfaced with a high-vacuum/high-pressure line. The reactor was evacuated to ~$10^{-3}$ Torr, then charged with the desired pressure of $H_2$ (typically 18 atm) at room temperature. The reactor was heated to the desired temperature and the reaction temperature and stirring (200-1900 rpm) was started to initiate the reaction. If the reaction was carried out at higher than 150° C., slow stirring (~200 rpm) was imitated until the desired temperature was reached (typically 5-10 minutes). The reaction was allowed to proceed for the desired time interval. The time interval is defined to begin when stirring is initiated. After the time interval lapsed, stirring was stopped, the reactor was removed from the furnace, and cooled using forced-air cooling. The reactor was depressurized, and a headspace sample was taken, if needed. The reaction mixture was worked up as described in the general polymer hydrogenolysis procedure.

General Polyolefin Hydrogenolysis Procedure with Toluene Swelling

The reactor was charged with polyolefin and SOC as describe in the general polyolefin hydrogenolysis procedure with AlS/$ZrNp_2$. Dry toluene (0.5-2.0 mL) was also added to the reactor. The reactor was sealed and removed from the glovebox. The reactor was heated to the desired temperature with slow stirring for ~30 minutes. The toluene was removed under reduced pressure (~$10^{-6}$ torr), then the reactor was charged with desired pressure of $H_2$. The reaction was carried out and worked up as described in the general polymer hydrogenolysis procedure.

Gas Phase NMR Experiment

A PTFE-sealed NMR tube was charged with 41.50 mg of catalyst. The tube was interfaced with a high-pressure/high-vacuum line and evacuated to ~$10^{-6}$ Torr. The tube was charged with 1 atm $H_2$, then sealed (internal volume~2.9 mL). NMR spectra were taken in 10-minute intervals. Between these 10-minute intervals, the NMR tube was removed from the magnet, then shaken for ~2 minutes. After 90 minutes, the NMR tube was heated to 150° C. for 30 minutes to drive the reaction to completion. A final spectrum was acquired after this to confirm that methane and ethane were the only hydrocarbons present. $^1H$ NMR measurements were taken using a Bruker Avance III (600 MHz) equipped with BBFO Smart Probe. The following acquisition parameters were used for obtaining gas-phase NMR spectra: acquisition time: 0.5 s, delay time: 20 s.

Activity Calculation for Polyolefin Hydrogenolysis Experiments

Activities for polyolefin hydrogenolysis are calculated as follows: 1.) Reaction products are taken to have a molecular weight of 14.026 g·mol$^{-1}$ (—$CH_2$— units) and include only the "volatiles" and "DCM extract" fractions. 2.) The molar quantity of products is divided by the number of moles of Zr added to the reaction. 3.) The resulting number is divided by the amount of time (in hours) the reaction was allowed to proceed. The resulting number is the activity for a polymer hydrogenolysis reaction, expressed in the following units: volatiles and DCM extract mol $CH_2$·mol $Zr^{-1}$·$h^{-1}$.

For a reaction producing 0.5 g DCM extract and volatiles combined, with 0.1 g SOC (1.4 wt % Zr present in SOC), allowed to proceed for 45 min, the activity is calculated as follows:

$$0.5\ g/14.026\ g\cdot mol^{-1}=0.0356\ mol\ —CH_2—\ units.$$

0.1 g SOC contains 0.0014 g Zr: 0.0014 g Zr/91.22 g·mol$^{-1}$ Zr=$1.535\cdot10^{-5}$ mol Zr added to reaction.

$$(0.0356\ mol\ —CH_2—\ units)/(1.535\cdot10^{-5}\ mol\ Zr)\cdot(0.75\ h)=3097\ mol\ —CH_2—\ units\cdot mol\ Zr^{-1}\cdot h^{-1}.$$

Table 16 provides hydrogenolysis activity data for Dow® polyethylene resins, carried out in a glass reactor as described above. Conditions for the reaction were: 200° C., 0.3 g SOC, 1.0 g polyethylene, 2 atm $H_2$. Reactions were carried out until a significant amount of the starting polymer was consumed by visual determination.

TABLE 16

Hydrogenolysis activity data for the indicated DOW ® polyethylene resins

| DOW ® Polymer Product | Reaction Time (min) | Activity (mol $CH_2$ units · mol $Zr^{-1}$ · $h^{-1}$) |
|---|---|---|
| Engage ™ 8402 | 25 | 3302 |
| Engage ™ 8450 | 50 | 1876 |
| Affinity ™ 1850-G | 120 | 772 |
| Affinity ™ GA-1900 | 15 | 5274 |

Table 17 provides hydrogenolysis activity data for Dow® polyethylene resins, carried out in a Parr reactor (25 mL) as described above. Conditions for the reaction were: 200° C., 0.03 g catalyst, 1.0 g polyethylene, 18 atm $H_2$ (reactor charged at 30° C.). Reactions were carried out until a significant amount of the starting polymer was consumed by visual determination.

TABLE 17

Hydrogenolysis activity data for DOW ® polyethylene resins in a Parr reactor with rapid stirring

| DOW ® Polymer Product | Stirring Rate (RPM) | Reaction Time (min) | Activity (mol $CH_2$ units · mol $Zr^{-1}$ · $h^{-1}$) |
|---|---|---|---|
| Engage ™ 8402 | 1900 | 20 | 36568 |
| Engage ™ 8402 | 400 | 40 | 12431 |
| Affinity ™ 1850-G | 400 | 60 | 7929 |
| Affinity ™ GA-1900 | 1900 | 20 | 35474 |

Figure 7:
FIG. 7 shows the product distribution (volatile, DCM extract and solids product) for hydrogenolysis of the indicated polyolefins in Table 17 at various stirring rates.
Figure 7:
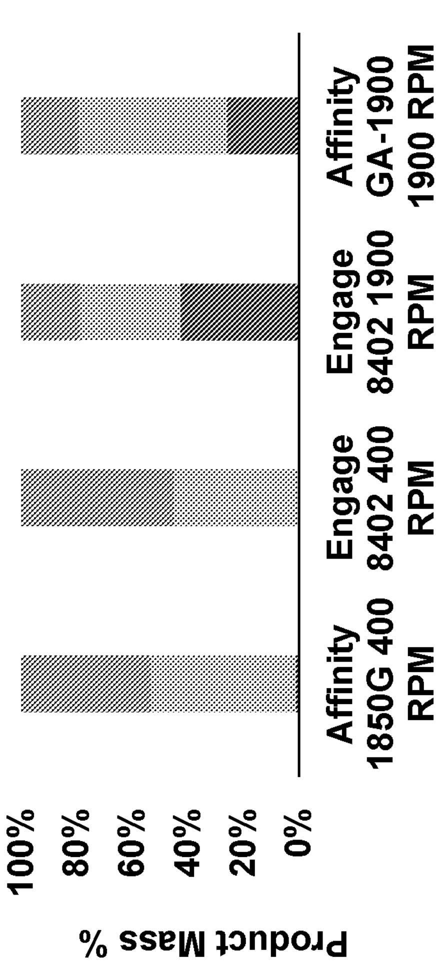
Figure 8:
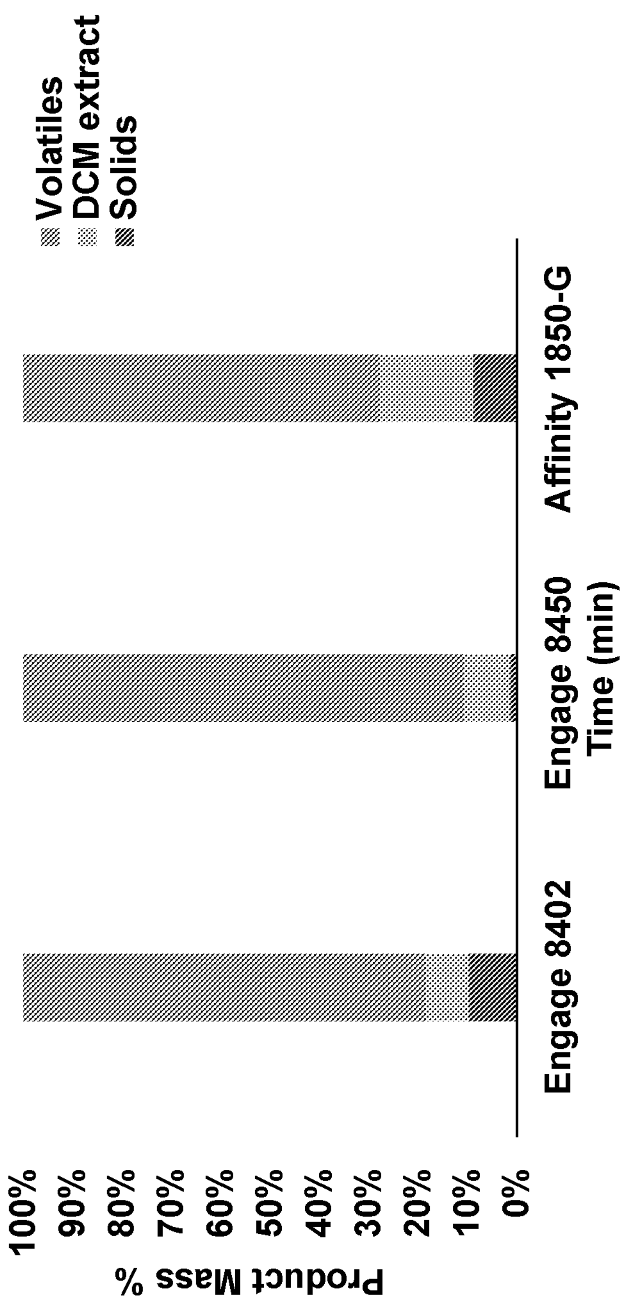
FIG. 8 shows the mass percent of the volatile, DCM extract and solids product for the reduced polymer product of Table 17.

Product distribution for hydrogenolysis of the polymer products (volatiles, DCM extract and solids products) in Table 17 for stirring rate are seen in FIG. 7. For the reaction conditions provided for Table 17, product distribution (volatiles, DCM extract and solids products) for hydrogenolysis of Engage™ 8402, Engage™ 8450 and Affinity™ 1850-G for reaction time is seen in FIG. 8.

Table 18 provides hydrogenolysis activity data for commercial polyethylene resins with toluene swelling carried out in a 350 mL glass reactor with magnetic stir bar as described above. Conditions for the reaction were: 200° C., 0.1 g catalyst (0.0014 g Zr) used per reaction, 1.0 g commercial polyethylene resin, 2 atm $H_2$. Reactions were carried out until a significant amount of the starting polymer was consumed by visual determination.

TABLE 18

Hydrogenolysis activity data for commercial polyethylene resins with toluene swelling

| Polymer Product | Reaction Time (min) | Activity (mol $CH_2$ units · mol $Zr^{-1}$ · $h^{-1}$) |
|---|---|---|
| Engage ™ 8402 | 50 | 3458 |
| Milk Jug | 31 | 6058 |
| HDPE Fruit Pouch Cap | 138 | 682 |

Figure 9:
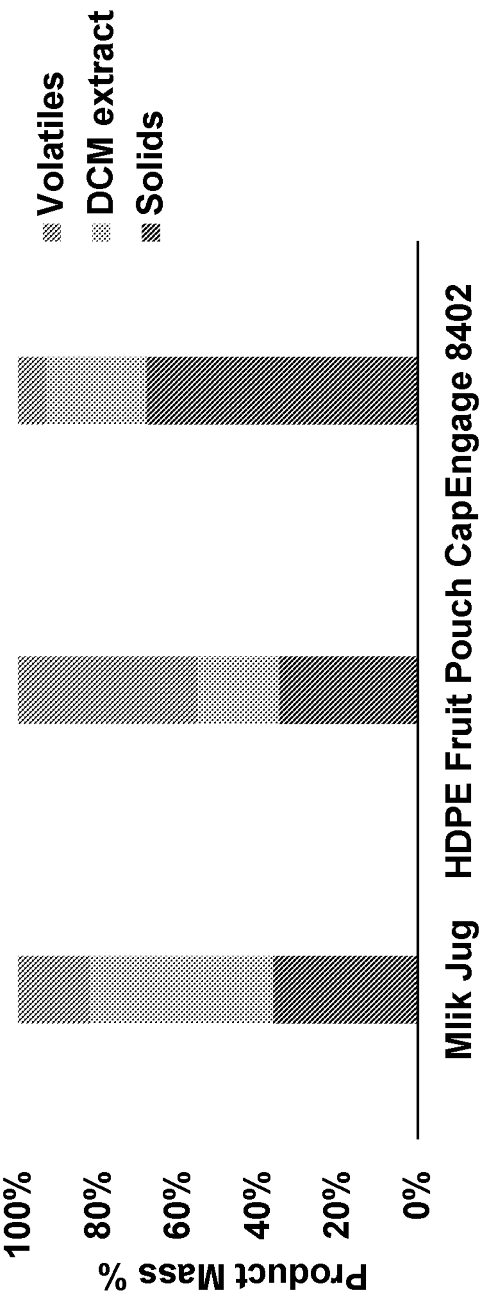
FIG. 9 shows the product distribution (volatile, DCM extract and solids product) for hydrogenolysis of the indicated polyolefins for the given reaction conditions of Table 18.

For the reaction conditions provided for Table 18, product distribution (volatiles, DCM extract and solids products) for hydrogenolysis of Engage™ 8402, Milk Jug and HDPE Fruit Pouch Cap is seen in FIG. 9.

The word “illustrative” is used herein to mean serving as an example, instance, or illustration. Any aspect or design described herein as “illustrative” is not necessarily to be construed as preferred or advantageous over other aspects or designs. Further, for the purposes of this disclosure and unless otherwise specified, “a” or “an” means “one or more.”

If not already included all numeric values of parameters in the present disclosure are proceeded by the term “about” which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the invention in various embodiments and with various modifications as suited to the particular use contemplated. It is intended that the scope of the disclosure be defined by the

What is claimed is:

1. A process for hydrogenolysis of a polymer, comprising:

providing in a reactor the polymer, hydrogen gas and a supported organometallic catalyst, the supported organometallic catalyst formed from an organometallic complex precatalyst of Formula I:

$MR_mL_x$, Formula I wherein m is 0 to 6; x is 0 to 6; M is a transition metal selected from the group consisting of transition metal groups 3 through 8; R is independently selected from the group consisting of H, a C1 to C8 hydrocarbyl, and a halogen; and each L is independently selected from the group consisting of a C1 to C12 substituted or unsubstituted hydrocarbyl, wherein the value of m and x depends upon the oxidation state of M; and an acidic metal oxide support; and reacting the polymer with the supported organometallic catalyst in the presence of the hydrogen gas at a predetermined temperature in the reactor to produce a reduced polymer product having a weight average molecular weight less than the polymer, wherein the supported organometallic catalyst is represented by Formula II:

$L_{y-x}R_{x-z}M^{n+}$ . . . $O^-$ (acidic metal oxide support) Formula II wherein M is selected from the group consisting of Zr, Hf, Ti, Nb, V, Cr, Mo, W. Ta, Co, and Ni; R is independently selected from hydrogen, a halogen, and L; each L is independently selected from a C1 to C12 saturated or unsaturated hydrocarbyl, and a C1 to C12 silyl hydrocarbyl; n is 1, 2, or 3; y is 3; x is 2 or 1; and z is 1 or 0.

2. The process of claim 1, wherein M is selected from the group consisting of transition metal groups 4, 5, 6 and 8.

3. The process of claim 2, wherein M is selected from the group consisting of Ti, Zr, Hf, V, Nb, Ta, Cr, Mo, W, Fe, Ru, Co and Ni.

4. The process of claim 1, wherein the hydrocarbyl for L is independently selected from the group consisting of a C1 to C10 alkyl, a C2 to C10 alkenyl, and a C5 to C10 aryl.

5. The process of claim 1, wherein the predetermined temperature is from 60° C. to 300° C.

6. The process of claim 1, wherein the reduced polymer product is at least one of a volatile product, an oil product or a wax product.

7. The process of claim 6, wherein the reduced polymer product includes less than 5 weight percent of the wax product based on the total weight of the reduced polymer product.

8. The process of claim 1, wherein the polymer is selected from the group consisting of a polyolefin, a polymer formed by polymerization of aromatic alkenes, and those formed by polymerization of conjugated dienes.

9. The process of claim 8, wherein the polyolefin is selected from the group consisting of polyethylene, polypropylene, a linear or branched C4-C12 mono-olefin, a copolymer thereof, and combinations thereof.

10. The process of claim 1, wherein M is Zr or Hf; m is 0, and each L is independently selected from the C1 to C12 alkyl.

11. The process of claim 10, wherein L is neopentyl.

12. The process of claim 1, wherein the acidic metal oxide support is a sulfated metal oxide.

13. The process of claim 12, wherein the sulfated metal oxide is selected from the group consisting of a sulfated aluminum oxide, zirconium (IV) oxide, tin (IV) oxide, hafnium (IV) oxide, titanium (IV) oxide; iron (III) oxide, zinc (II) oxide; silica oxide, and combinations thereof.

14. The process of claim 1, wherein M is selected from the group consisting of Ti, Zr, and Hf; each L is a C3-C8 saturated or unsaturated hydrocarbyl, and x is 1 and z is 1.

15. The process of claim 1, wherein providing hydrogen gas to the reactor includes providing the hydrogen gas at a pressure of 0.1 atm to 100 atm to the reactor.

16. The process of claim 1, wherein reacting the polymer includes stirring the polymer with the supported organometallic catalyst in the presence of the hydrogen gas at a rate of 500-3000 rpm.

17. The process of claim 1, wherein reacting the polymer with the supported organometallic catalyst in the presence of the hydrogen gas at the predetermined temperature is for a time from 0.25 hour to 24 hours.

18. The process of claim 1, wherein providing in the reactor the supported organometallic catalyst includes providing from 0.01 mole percent (mol. %) to 0.9 mol. % of M based on the monomer units of the polymer.

19. A process for hydrogenolysis of a polymer, comprising:

providing in a reactor the polymer, hydrogen gas and a supported organometallic catalyst, the supported organometallic catalyst formed from an organometallic complex precatalyst of Formula I:

$$MR_mL_x, \quad \text{Formula I}$$

wherein m is 0 to 6; x is 0 to 6; M is a transition metal selected from the group consisting of transition metal groups 3 through 8; R is independently selected from the group consisting of H, a C1 to C8 hydrocarbyl, and a halogen; and each L is independently selected from the group consisting of a C1 to C12 substituted or unsubstituted hydrocarbyl, wherein the value of m and x depends upon the oxidation state of M; and an acidic metal oxide support; and reacting the polymer with the supported organometallic catalyst in the presence of the hydrogen gas at a predetermined temperature in the reactor to produce a reduced polymer product having a weight average molecular weight less than the polymer, wherein the supported organometallic catalyst is represented by Formula II:

$$L_{y-x}R_{x-z}M^{n+}\ \underline{...}\ O^{-}\ \text{(acidic metal oxide support)} \quad \text{Formula II}$$

wherein M is selected from the group consisting of Zr, Hf, Ti, Nb, V, Cr, Mo, W, Ta, Co, and Ni;

R is independently selected from hydrogen, a halogen, and L; each L is independently selected from a C1 to C12 saturated or unsaturated hydrocarbyl, and a C1 to C12 silyl hydrocarbyl; n is 1; y is 3; x is 2 or 1; and z is 1 or 0.

* * * * *